US008900416B2

(12) United States Patent
Hilten et al.

(10) Patent No.: US 8,900,416 B2
(45) Date of Patent: Dec. 2, 2014

(54) PRODUCTION OF HIGHER QUALITY BIO-OILS BY IN-LINE ESTERIFICATION OF PYROLYSIS VAPOR

(75) Inventors: Roger Norris Hilten, Winterville, GA (US); Keshav Das, Athens, GA (US); James R. Kastner, Athens, GA (US); Brian P. Bibens, Houston, TX (US)

(73) Assignee: University of Georgia Research Foundation, Inc., Athens, GA (US)

( * ) Notice: Subject to any disclaimer, the term of this patent is extended or adjusted under 35 U.S.C. 154(b) by 631 days.

(21) Appl. No.: 13/139,383

(22) PCT Filed: Feb. 22, 2010

(86) PCT No.: PCT/US2010/024887
§ 371 (c)(1),
(2), (4) Date: Jun. 13, 2011

(87) PCT Pub. No.: WO2010/099058
PCT Pub. Date: Sep. 2, 2010

(65) Prior Publication Data
US 2011/0296745 A1    Dec. 8, 2011

Related U.S. Application Data

(60) Provisional application No. 61/154,863, filed on Feb. 24, 2009.

(51) Int. Cl.
*C10G 3/00* (2006.01)
*C10L 1/02* (2006.01)
(Continued)

(52) U.S. Cl.
CPC . *C10L 1/02* (2013.01); *C10B 47/44* (2013.01); *C10L 1/19* (2013.01);
(Continued)

(58) Field of Classification Search
CPC ........... C10B 47/44; C10G 1/02; C10G 3/00; C10G 5/00; C10G 2300/1011; C10L 1/02; C10L 1/19; C10L 1/224; C10L 2200/0469; C10L 2290/02; C10L 2290/18; C10L 2290/141; Y02E 50/14
USPC ............... 201/25, 29; 202/118; 585/240–242; 44/310, 388, 418, 436, 605; 422/187
See application file for complete search history.

(56) References Cited

U.S. PATENT DOCUMENTS 5,064,623 A * 11/1991 Harandi et al. ............... 422/618
5,426,199 A *  6/1995 Lundquist ..................... 554/169
(Continued)

FOREIGN PATENT DOCUMENTS

WO        2006119219 A2    11/2006
WO        2007068097 A1     6/2007
(Continued)

OTHER PUBLICATIONS

The International Search Report and Written Opinion dated Oct. 19, 2010.

*Primary Examiner* — Nina Bhat
*Assistant Examiner* — Jonathan Miller
(74) *Attorney, Agent, or Firm* — Thomas|Horstemeyer, LLP

(57) ABSTRACT

The disclosure encompasses in-line reactive condensation processes via vapor phase esterification of bio-oil to decease reactive species concentration and water content in the oily phase of a two-phase oil, thereby increasing storage stability and heating value. Esterification of the bio-oil vapor occurs via the vapor phase contact and subsequent reaction of organic acids with ethanol during condensation results in the production of water and esters. The pyrolysis oil product can have an increased ester content and an increased stability when compared to a condensed pyrolysis oil product not treated with an atomized alcohol.

28 Claims, 16 Drawing Sheets

(51) Int. Cl.
*C10B 47/44* (2006.01)
*C10L 1/19* (2006.01)
*C10L 1/224* (2006.01)
*C10G 1/02* (2006.01)
*C07C 67/08* (2006.01)

(52) U.S. Cl.
CPC . *C10L 1/224* (2013.01); *C10G 1/02* (2013.01); *C10G 3/00* (2013.01); *C07C 67/08* (2013.01); *C10L 2290/141* (2013.01); *C10L 2200/0469* (2013.01); *C10L 2290/18* (2013.01); *C10L 2290/02* (2013.01); *Y02E 50/14* (2013.01); *C10G 2300/1011* (2013.01)
USPC ............... 201/25; 201/29; 202/118; 44/310; 44/388; 44/418; 44/436; 44/605; 422/187

(56) References Cited

U.S. PATENT DOCUMENTS

| | | | |
|---|---|---|---|
| 5,792,340 A * | 8/1998 | Freel et al. | 208/127 |
| 7,507,846 B2 * | 3/2009 | Pelly | 554/170 |
| 8,420,841 B2 * | 4/2013 | Mann | 554/169 |
| 8,603,199 B2 * | 12/2013 | Steele et al. | 44/310 |
| 2007/0033863 A1 * | 2/2007 | Butler | 44/451 |
| 2007/0167642 A1 | 7/2007 | Oku et al. | |
| 2007/0261296 A1 * | 11/2007 | Adams et al. | 44/605 |
| 2009/0054711 A1 * | 2/2009 | Lawrence et al. | 585/240 |
| 2011/0054200 A1 * | 3/2011 | Cai et al. | 554/169 |

FOREIGN PATENT DOCUMENTS

| | | | | |
|---|---|---|---|---|
| WO | 2007127059 A2 | 11/2007 | | |
| WO | 2008020047 A2 | 2/2008 | | |
| WO | WO2010002236 | * | 1/2010 | C11C 3/10 |

* cited by examiner

PRODUCTION OF HIGHER QUALITY BIO-OILS BY IN-LINE ESTERIFICATION OF PYROLYSIS VAPOR

CROSS REFERENCE TO RELATED APPLICATION

This application claims priority to "PRODUCTION OF HIGHER QUALITY BIO-OILS BY IN-LINE ESTERIFICATION OF PYROLYSIS VAPOR" having serial number PCT/US2010/024887, filed on Feb. 22, 2010. This application also claims priority to and benefit of U.S. Provisional Application No. 61/154,863, filed on Feb. 24, 2009, which is incorporated by reference in its entirety.

STATEMENT REGARDING FEDERALLY SPONSORED RESEARCH OR DEVELOPMENT

This invention was made with government support under Grant No. DE-FG36-05GO85012 awarded by the Department of Energy of the United States government. The government has certain rights in the invention.

TECHNICAL FIELD

The present disclosure is generally related to a process for conversion of carboxylic acids of bio-oils to esters.

BACKGROUND

Bio-oil is a potential renewable energy source for electricity and heat generation as well as being an alternative transportation fuel. However, several hurdles must be crossed before bio-oil can be used reliably. One of the main issues is storage stability of the oils. During storage, there is potential for bio-oils to undergo changes due to oxidative and thermal degradation. Oxidation can lead to polymerization and significantly increased viscosity. Thermal degradation causes partial decomposition of bio-oil constituents and can lead to the loss of volatiles. Both degradative factors can lead to viscosity and compositional changes (Diebold & Czernik (1997) *Energy Fuels* 11: 1081-1091; Diebold, J. P. (1999) NREL/SR-570-27613; Oasmaa & Kuoppala, (2003) *Energy Fuels* 17: 1075-1084; Boucher et al., (2000) *Biomass Bioenergy* 19: 351-361).

Most applications for bio-oils require that bio-oils retain the favorable initial physical properties during storage, shipment and use (Diebold, 1999) to avoid the risk that filters, injectors, input lines, etc, may become obstructed. In addition, the high level of reactive species and water content of bio-oil makes it unstable under normal storage conditions, which leads to increased viscosity. In addition, high oxygen and water content also lower the heating value of the fuel (Oasmaa & Kuoppala, (2003) *Energy Fuels* 17: 1075-1084).

During the aging process, bio-oil viscosity and the chemical composition changes dramatically, mainly due to polymerization reactions (Adjaye et al., (1992) *Fuel Processing Technol.* 31: 241-256). A higher degree of polymerization results in an increase in viscosity. Polymerization reactions that lead to viscosity increases are accelerated at higher storage temperatures and it has been shown that the rate of change in viscosity can increase from 0.009 cP/day when stored at −20° C. to more than 300 cP/day at 90° C. (Adjaye et al., (1992) *Fuel Processing Technol.* 31: 241-256). Adding solvents after pyrolysis can increase the stability of bio-oil during aging. Diebold & Czernik ((1997) *Energy Fuels* 11: 1081-1091) showed that solvent addition could significantly decrease viscosity changes during aging. Solvents used in the study included ethyl acetate, methyl isobutyl ketone and methanol, acetone, methanol, acetone and methanol, and ethanol. Their findings showed that methanol at 10 wt % enhanced bio-oil stability most effectively, and reported a reduction in the rate of change in viscosity.

The immediate effects of adding an alcohol are decreased viscosity and increased heating value (Oasmaa et al., (2004) *Energy and Fuels* 18: 1578-1583; Moens et al., (2009) *Energy Fuels* 23: 2695-2699; Stamatov et al., (2006) *Renewable Energy* 31: 2108-2121). These improvements to bio-oil made it more favorable for combustion applications such as in furnaces, boilers and gas turbines, or as an alternative to diesel where untreated bio-oils can require major changes in current systems (Gust S., (1997) In: Bridgewater & Boocock., eds: *Developments in thermal biomass conversion*. London: Blackie Academic & Professional pp 481-488; Stamatov et al., (2006) *Renewable Energy* 31: 2108-2121). The increase in heating value for bio-oils mixed with ethanol is due to the fact that ethanol has a high heating value of 27 MJ kg$^{-1}$, which is higher than that of most bio-oils.

Most studies have directly added alcohols after pyrolysis (Moens et al., (2009) *Energy Fuels* 23: 2695-2699; Oasmaa et al., (2004) *Energy and Fuels* 18: 1578-1583, Diebold & Czernik ((1997) *Energy Fuels* 11: 1081-1091) which works well to increase stability and heating value. However, several recent studies (Zhang et al., (2006) *Energy & Fuels* 20: 2717-2720; Tang et al., (2008) *Energy Fuels* 22: 3484-3488; Mahfbd et al., (2007) *Transactions of the Institution of Chemical Engineers Part B* 85, 466-472; Chang et al., (2007) *Chinese Chemical Letters,* 18: 445-447; Junming et al., (2008) *Biomass and Bioenergy* 32: 1056-1061; Lu et al., *Chin. Chem. Lett.* (2007) 18: 445-447), showed that using reactive distillation of bio-oil with alcohol along with an acid or base catalyst, esterification of bio-oil was possible. Esterifying bio-oil can significantly improve the quality of bio-oil by lowering water content, viscosity and free-acid content. Additional improvements in bio-oil quality include an increase in heating value by as much as 50% (Junming et al., (2008) *Biomass and Bioenergy* 32: 1056-1061; Zhang et al, (2006) *Energy Fuels* 20: 2717-2720) and an increase in stability due to the removal of acids that catalyze many polymerization reactions. Junming et al. (2008) showed that after three months of aging, esterified bio-oil exhibited very little viscosity increase. Ji-lu et al. (*J. Anal. Appl. Pyrolysis* (2007) 80: 30-35) introduced well-sprayed ethanol into a bio-oil condenser as a precursor to spraying bio-oil once enough was produced. The intent was to quickly cool vapors to prevent polymerization reactions, though esterification was not observed.

Fischer esterification is proposed to be the reaction pathway in conversion to esters. The esterification reaction follows the equation:

$$RCOOH + C_nH_{2n+1}OH \leftrightharpoons RCOOC_nH_{2n+1} + H_2O,$$

leading to the formation of water and an ester. The simplest ester that can be produced is methyl formate, $HCOOCH_3$, when methanol ($CH_3OH$) is used as the alcohol and is reacted with formic acid, $HCOOH$. Industrially the reaction is always catalyzed by a strong acid. Several studies (Junming et al., (2008) *Biomass and Bioenergy* 32: 1056-1061; Tang et al., (2008) *Energy Fuels* 22: 3484-3488) have used solid acid catalysts to enhance the bio-oil esterification reaction which improved bio-oil quality by increasing HHV and pH and reducing specific gravity, viscosity and water content for esterified bio-oil.

Esterification reactions are not, however, intended to be limited to linear, alkyl, saturated alcohols or acids. For example, and not intended to be limiting, branched alcohols such as tert-Bu-$C_nH_{2n+1}$OH) and acids (e.g., iso-Pr-$C_nH_{2n+1}$COOH), (poly)unsaturated species (e.g., $CH_3HC=CHC_nH_{2n+1}$OH and $CH_3HC=CHC_nH_{2n+1}$COOH), and aromatic compounds such as, but not limited to, $C_6H_5$OH, $C_6H_5CH_2$OH, and $C_6H_5$COOH, and the like may also be used to carry out esterification reactions according to the present disclosure.

Several studies (Chu et al., (1996) *Appl. Catal., A: General* 145: 125-140; Kirumakki et al., (2006) *Appl. Catal., A: General* 299: 185-192; Koster et al., (2001) *J. Catal.* 204: 333-338; Miao & Shanks (2009) *Appl. Catal., A: General* 359: 113-120) have shown the potential to use heterogeneous catalysts for esterifying model bio-oil compounds such as acetic acid. As an example, Miao & Shanks ((2009) *Appl. Catal., A: General* 359: 113-120) esterified acetic acid, a model bio-oil compound, using a mesoporous catalyst. Acetic acid conversion was close to 40% at a 250 min reaction time at 50° C. using the catalyst. Zhang et al., ((2006) *Energy Fuels* 20: 2717-2720) esterified acetic acid in a reflux reactor and showed yields ranging from 15% (no catalyst) to 100% (solid acid catalyst). Koster et al., ((2001) *J. Catal.* 204: 333-338) and Chu et al., ((1996) *Appl. Catal., A: General* 145: 125-140) performed vapor-phase esterifications of acetic acid with ethanol. Koster et al., (2001) performed gas-phase esterifications over several mesoporous catalysts, and showed moderate ester yields (<25%). Equilibrium for the reaction lies far to the right, especially in the vapor phase, for which the thermodynamic equilibrium constant is 367 for the reaction of ethanol and acetic acid to form ethyl acetate.

SUMMARY

Briefly described, embodiments of this disclosure encompass in-line reactive condensation processes via vapor phase esterification of bio-oil to decrease reactive species concentration and water content in the oily phase of a two-phase oil, thereby increasing storage stability and heating value. Esterification of the bio-oil vapor occurs via the vapor phase contact and subsequent reaction of organic acids with ethanol during condensation results in the production of water and esters.

One aspect of the present disclosure, therefore, encompasses methods of modifying the content of a pyrolysis oil product, comprising: (a) treating a pyrolysis oil vapor comprising a carbonyl-containing component with an atomized alcohol or amine under conditions allowing a condensation reaction between the carbonyl-containing component and the alcohol or amine, thereby generating a reaction product; and (b) condensing the pyrolysis oil vapor and the reaction product to form a pyrolysis oil product having an increased ester or amide content when compared to a condensed pyrolysis oil product not treated with an atomized alcohol or amine.

In embodiments where the pyrolysis oil vapor is treated with an atomized alcohol, the condensation reaction is an esterification, and the reaction product is an ester.

In embodiments where the pyrolysis oil vapor is treated with an atomized amine, the reaction product is an amide.

In some embodiments, the in the condensation reaction can proceed in the absence of a catalyst.

In embodiments of this aspect of the disclosure, the pyrolysis oil product can have an increased stability when compared to a condensed pyrolysis oil product not treated with an atomized alcohol or amine.

Another aspect of the disclosure provides a process for generating a pyrolysis oil product, comprising: pyrolyzing a biomass, thereby generating a heated pyrolysis oil vapor comprising at least one carbonyl-containing component; delivering the pyrolysis oil vapor to a reactive condensation unit, delivering an atomized alcohol to the reactive condensation unit, thereby forming a reaction mix comprising the pyrolysis oil vapor and the atomized alcohol or amine; maintaining the reaction mix under conditions suitable for generating at least one condensation reaction product in the absence of a catalyst; and condensing the pyrolysis oil vapor and the at least one condensation reaction product to form a pyrolysis oil product having an increased ester or amide content and increased stability when compared to a condensed pyrolysis oil product not treated with an atomized alcohol or amine.

Yet another aspect of the present disclosure provides a pyrolysis oil product having a decreased carboxylic acid content and increased stability when compared to a pyrolysis oil product not treated with an atomized alcohol or amine according to the processes of the disclosure.

Still yet another aspect of the disclosure provides systems for generating a pyrolysis product, comprising: a pyrolysis unit configured to receive and pyrolyze a biomass, thereby generating a heated pyrolysis oil vapor having a carbonyl-containing component; a reactive condensation unit operably communicating with the pyrolysis unit, wherein the reactive condensation unit is configured to receive the pyrolysis oil vapor and an atomized alcohol or amine, thereby forming a reaction mix within the reactive condensation unit, and further configured to deliver a condensate to a receiving vessel; and a receiving vessel operably disposed to receive a condensate comprising a pyrolysis oil product from the reactive condensing unit.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
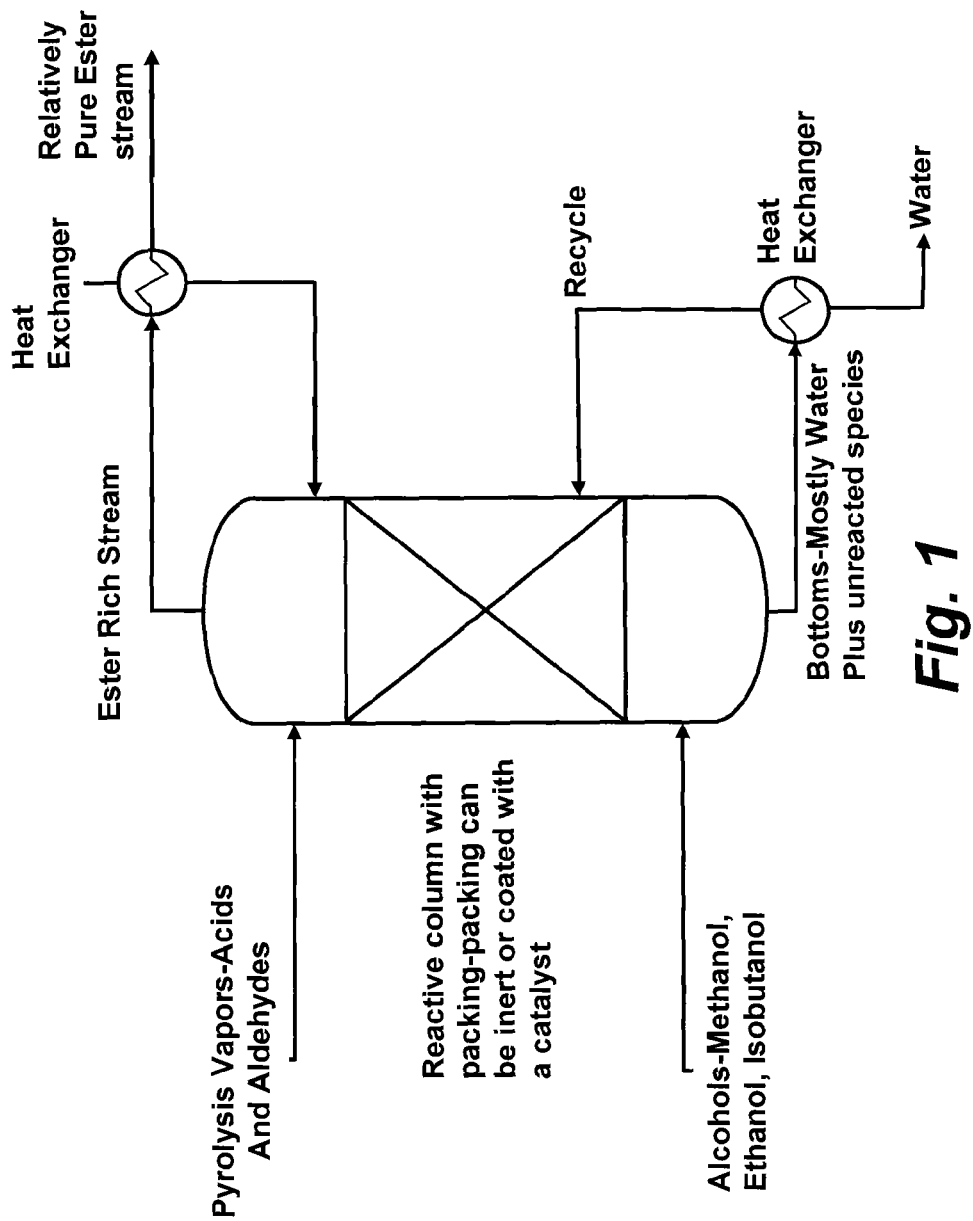
FIG. 1 shows a schematic of the integration of pyrolysis with reactive distillation and esterification (catalytic or non-catalytic) and using the biomass pyrolysis oil vapors to form stable bio-oil (a counter-current scheme is portrayed where pyrolysis vapors and the alcohol vapor move in opposite directions).

The drawings are described in greater detail in the description and examples below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support"

includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing and claiming the disclosed subject matter, the following terminology will be used in accordance with the definitions set forth below.

The terms "pyrolysis oil", "pyrolysis oil product", and "bio-oil" as used herein refer to a synthetic fuel extracted by biomass-to-liquid technologies of destructive distillation from dried biomass in a reactor at temperature of about 500° C. with subsequent cooling of the issuing vapors. The treated biomass is split into solid and gaseous components under the influence of heat only (anhydrous pyrolysis). The produced charcoal (char) may also be used for heating the process, used as a soil additive biochar, or as activated carbon in absorption processes. The non-condensable gas, consisting of hydrogen, carbon monoxide, carbon dioxide, and methane may be burned. The condensable gases (vapors) may be rapidly cooled to form condensate droplets which can then be separated from the non-condensable gases due to the substantial difference in density of each fraction. The condensate may be reignited similar to a fossil fuel oil with a heating value is 15-22 MJ/kg.

The produced oil typically is acidic with a pH of 1.5-3.8 (average 2.8). The acidity may be lessened by the addition of readily available base compounds. Little work has been done on the stability of bio oil acidity changed with base compounds. While the biomass begins with 10% to 15% moisture, the oil does not end up with a water content. The water molecules are split during pyrolysis and held separately in other compounds within the complex pyrolysis liquid. "Water" in pyrolysis oil does not separate like standard fossil fuels. The density is approximately 1.2-1.3 (1.22) kg/L or 10.01-10.85 (10.18) lbs/gallon, which is higher than standard diesel. The oxygen content is 40-50%, mostly from the "water" content, and no sulfur may be detected normally. The lower heating value is approximately 16-21 (17.5) MJ/kg. The pour point is −12° C. to −33° C., no cloud point typically can be observed until −21° C. The carbon residue of pyrolysis oil is about 17 wt % to about 23 wt %, with a flash point of between about 40° C. and about 100° C. On storage of pyrolysis oils, the viscosity increases to a maximum in period of 12 months due to polymerization. The pyrolysis oil is not stable, reacting with air.

The term "carbonyl-containing component" as used herein refers to compounds comprising a carbonyl (C=O) group, including mono- and di-carboxylic acids, aldehydes, and ketones.

The terms "atomized" or "atomized alcohol" as used herein refers to a liquid that is dispersed as a stream or spray of fine droplets having been passed through a small nozzle. Typically, an atomizer nozzle is a kind of nozzle for producing a fine spray of a liquid based on the Venturi effect. When a gas is blown through a constriction it speeds up; this reducing the pressure at the narrowest point. The reduced pressure sucks up a liquid through a narrow tube into the flow, where it boils in the low pressure, and forms thousands of small droplets. In the systems of the present disclosure, the atomizer nozzle or inlet into a reactive condensation unit may be similar to a carburetor or spray nozzle.

The term "esterification reaction" as used herein refers to a chemical reaction in which two reactants (typically an alcohol and an acid) form an ester as the reaction product.

The terms "ester" and "ester reaction product" as used herein refer to compounds derived by reacting a carbonyl group, an oxoacid (one containing an oxo-group, X=O) with a hydroxyl compound such as an alcohol or phenol. Esters are usually derived from an inorganic acid or organic acid in which at least one —OH (hydroxyl) group is replaced by an —O-alkyl (alkoxy) group, and most commonly from carboxylic acids and alcohols.

The term aliphatic alcohol" as used herein refers to saturated C1-C20 chain alcohols that may be straight-chain or branched.

The term "primary alcohol, a secondary alcohol, or a tertiary alcohol" as used herein refer to alcohols based upon the number of carbon atoms connected to the carbon atom that bears the hydroxyl group. Namely, the primary alcohols have general formulas $RCH_2OH$; secondary ones are $RR'CHOH$; and tertiary ones are $RR'R''COH$, where R, R', and R'' stand for alkyl groups. Ethanol and n-propyl alcohol are primary alcohols; isopropyl alcohol is a secondary one. The prefixes sec- (or s-) and tert- (or t-), conventionally in italics, may be used before the alkyl group's name to distinguish secondary and tertiary alcohols, respectively, from the primary one. For example, isopropyl alcohol is occasionally called sec-propyl alcohol and the tertiary alcohol $(CH_3)_3COH$, or 2-methylpropan-2-ol in IUPAC nomenclature, is commonly known as tert-butyl alcohol or tert-butanol. Primary, secondary and tertiary alcohols for use in the methods of the disclosure may include, but are not limited to, unsaturated, display side chain or substituent containing a heteroatom such as, without limitation, S, a halogen, or O. Phenolic compounds such as $C_6H_5OH$ and napthyl-OH, will be considered alcohols. The terms "primary alcohol", "secondary alcohol", and "tertiary alcohol" as used herein also refer to terminal polyols, such as $HOCH_2CH_2OH$, $(HOCH_2)_3CH$, $HOCH_2CH(OH)CH_2OH$, and $(HOCH_2CH_2)_3COH$, and the like.

The term "carboxylic acid" as used herein refers to organic acids characterized by the presence of a carboxyl group, which has the formula —C(=O)OH, usually written —COOH or —$CO_2H$. Carboxylic acids are Brønsted-Lowry acids, i.e., they are proton donors. Exemplary carboxylic acids that may be esterified by the methods and processes of the disclosure include, but are not limited to formic acid, acetic acid, propionic acid, butyric acid, and the like. The term "carboxylic acid" as used herein may further include any aromatic, unsaturated, branched and heteroatom ligated species bearing the carboxyl group such as, but not limited to, compounds having the structural formulae of $C_6H_5COOH$, $CH_3CH=CHCH_2COOH$, tert-BuCH($^i$Pr)COOH, $CH_3CH_2CH(OCH_3)COOH$, and the like.

The term "amine" or "amino" as used herein encompasses compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The terms "alkylarylamino," "alkylaminoaryl" or "arylaminoalkyl" refer to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarbonyl" as used herein refers to compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are also considered included in term "amide." Amides also include urea groups (aminocarbonylamino) and carbamates (oxycarbonylamino).

The term "a phenol and/or a polyphenol" encompasses any compound having a hydroxyl moiety bonded to an aromatic ring structure, wherein the ring structure can have one or more aromatic rings in the structure and may be further substituted with other substituents. Examples of phenols include, but are not limited to aminophenols and phenols substituted with an aliphatic residue like allylphenol such as, for example, phenol, napthol, 1-hydroxyanthracene, 2-hydroxyanthracene, 1,4-dihydroxyanthracene, 1-hydroxyphenanthrene, 1-hydroxypyrene, hydroxybenzopyrene, hydroxypentacene, hydroxynaphtacene, hydroxychrysene.

The term "biochar" as used herein refers to charcoal created by pyrolysis of biomass. The term "pyrolyzing a biomass" as used herein refers to obtaining gaseous or vaporous products by heating a biomass. The yield of products from pyrolysis varies heavily with temperature. The lower the temperature, the more char is created per unit biomass. High temperature pyrolysis is also known as gasification, and produces primarily syngas from the biomass. The two main methods of pyrolysis are "fast" pyrolysis and "slow" pyrolysis. Fast pyrolysis yields about 60% bio-oil, about 20% biochar, and about 20% syngas, and can be done in seconds. Slow pyrolysis can be optimized to produce substantially more char (about 50%), but can take hours to complete.

The term "biomass" as used herein refers to biological material derived from living, or recently living organisms, such as wood, waste, and alcohol fuels. Biomass is commonly plant matter grown to generate electricity or produce heat. For example, forest residues (such as dead trees, branches and tree stumps), yard clippings and wood chips may be used as biomass. However, biomass also includes plant or animal matter used for production of fibers or chemicals. Biomass may also include biodegradable wastes that can be burnt as fuel. Industrial biomass can be grown from numerous types of plant, including miscanthus, switchgrass, hemp, corn, poplar, willow, sorghum, sugarcane, and a variety of tree species, ranging from eucalyptus to oil palm (palm oil). The particular plant used is usually not important to the end products, but it does affect the processing of the raw material.

The term "cloud point" as used herein refers to the temperature at which dissolved solids are no longer completely soluble in a fluid, precipitating as a second phase giving the fluid a cloudy appearance.

DESCRIPTION

The present disclosure provides methods, processes and systems for generating pyrolysis oil (bio-oil) having a decreased carboxylic acid content. The methods of the present disclosure provide for condensation reactions between heated pyrolysis oil vapor and an atomized alcohol or amine, whereby the carboxylic acid products of the pyrolysis procedure are converted to corresponding esters or amides. The reduction in the content of carbonyl compounds, and in particular of carboxylic acids, of the pyrolysis oil vapor provides a condensed oil product that has increased stability and heat value when compared to condensed pyrolysis oil not so treated. By delivering an alcohol such as ethanol to a pyrolysis oil vapor, non-catalyzed esterification reactions are possible between some or all of the carbonyl component species of the vapor. These reactions occur during the condensation phase of the process, to yield a pyrolysis oil (bio-oil) product. Accordingly, the methods of the disclosure avoid the need for esterification by catalyzed reactions and provide a simple procedure to improve the storage stability and heat-yield properties of the bio-oil during the vapor condensation stage. It is, however, contemplated that a homogeneous acid catalyst, such as a mineral acid for example, may also be introduced in an atomized form to further enhance the rate of the esterification reaction. It is also contemplated that the reactive condensation unit may further include a heterogeneous acidic catalyst.

In the embodiments of the present disclosure, an alcohol or amine may be atomized into a stream of uncondensed bio-oil vapor to quickly cool and condense the vapors while simultaneously esterifying the resultant bio-oil. By so introducing esters or amines into the pyrolysis oil (bio-oil) there is an increase the quality of bio-oil by effectively removing undesired acidic compounds that would otherwise be present. The addition of an alcohol during the condensation of the vapors increases the stabilization of the bio-oil by quickly quenching bio-oil vapor to prevent secondary reactions and by simple dilution of reactive species before reactions can occur. In addition, carbonyl compounds including carboxylic acids such as, but not limited to, acetic acid and which occur in high concentrations in the pyrolysis oil vapor (Gayubo et al., (2004) *Energy and Fuels* 18: 1640-1647; Milne et al., 1997) undergo Fischer esterification upon mixing with ethyl alcohol at an elevated temperature to produce esters and water.

The formation of water should be evident in the overall water balance of pyrolysis. Due to the lower polarity of esters compared to carboxylic acids, the solubility of water in the oily phase of the bio-oil will be reduced. Thus, it is to be expected that water produced during esterification will be concentrated in the aqueous phase of the bio-oil and thereby reducing the water content of the oily phase. While not wishing to be bound by any one theory, acetylation likely occurs by the following the equation:

$$RCOH + C_2H_5OH \leftrightarrows RCH\text{—}OC_2H_5 + H_2O$$

Rapid condensation, esterification and acetylation will stabilize the bio-oil more effectively than simple condensation, thereby increasing thermal and oxidative stability.

The ability to produce esters from carbonyl components and in particular from carboxylic acids in bio-oil is a step in the development of fuel-quality pyrolysis oils. The present disclosure encompasses processes whereby an alcohol can be atomized into uncondensed bio-oil vapor at elevated temperatures, and providing a one-step combined condensation and esterification process without the need for a catalyst. Not only do the resulting esters improve quality when they remain in the oil, they can also be removed easily by distillation due to their higher volatility compared to the acids from which they are derived. Esters are highly valued products in the chemical industry. One example of their use is in the fabrication of a valuable class of polymers, the polyesters. When left in the bio-oil, esters increase heating value compared to the carboxylic acids they replace. Esterification of bio-oil may also reduce viscosity and acidity, while increasing stability of the oil. Increased stability is the result of the removal of acids that would otherwise catalyze condensation reactions that can lead to polymerization of bio-oil components. Further, esterification reduces the corrosive ability of bio-oils, by replacing the acidic hydrogen in the carboxyl group for a more inert alkyl-oxygen bond. Reduction of this corrosive ability also improves the safety to handle bio-oils.

An additional advantage of the methods of the present disclosure is that any alcohol may be used to condense and esterify the bio-oil vapor depending on what esters are desired as the end product. For example, but not intended to be limiting, if methanol, butanol or propanol is used, resulting esters will include, but are not limited to, methyl, butyl, or propyl acetate, respectively. Additionally due to the presence of other organic acids in the oils such as formic acid, propionic acid, and butyric acid, it is possible to produce esters including, but not limited to, formates, butyrates, and propionates in addition to acetate. The relative size of the esters determines the flash point and boiling point of the bio-oil produced. A bio-oil produced by condensation with methanol will have the lowest flash and boiling points. A disadvantage of longer chain alcohols is a significant reduction in the reaction rate. However, if an acidic catalyst is employed, the reaction rate can be increased if required.

The removal of organic acids from pyrolysis oils (bio-oils) is beneficial due to the fact that they may be precursors to coke formation on catalyst surfaces. In addition, the deoxygenation of carboxylic acids over zeolite catalysts is more difficult than with ketones or aldehydes. Esterifying organic acids prior to upgrading reduces the difficulty by removing oxygen in the form of water; esters compared to the acids that produced them have much lower oxygen content. For example, the elemental oxygen content of acetic acid is 53.3% w/w while for its corresponding ester, ethyl acetate if ethanol was used for the esterification, the oxygen content is 36.4% w/w. The further removal of oxygen from esters during catalytic upgrading is much easier. Thus, once catalytically upgraded, the resulting esterified bio-oil will be more like a hydrocarbon than if no esterification had been attempted.

Some embodiments of the processes of the disclosure operate as a reactive condensation process encompassing co-current operation (see FIGS. 1 and 2, for example) with condensation occurring particularly, but not exclusively, at the distal end of the reactor relative to inlet ports used for delivering the pyrolysis oil vapor and the atomized ethanol to the reactive condensation unit; such a continuous reactive distillation mode can result in 1) lower amounts of alcohol needed, 2) separation between the bio-oil phase and water, and 3) a higher quality bio-oil. In other embodiments, the alcohol and the pyrolysis oil vapor inlet ports are disposed in the reactive condensation unit to generate a counter-flow of one vapor against the other.

Embodiments of the methods, processes and apparatus of the present disclosure allow for improvements in the quality of bio-oil by coupling biomass pyrolysis with a reactive condensation step. By atomizing an alcohol into uncondensed bio-oil vapor produced during pyrolysis of a biomass, a single integrated step combining condensation and esterification processes has been developed. Using a reactive condensation unit, carbonyl-containing compounds in pyrolysis oil (bio-oil) vapor can be esterified with an atomized alcohol such as ethanol at elevated temperatures of about 114° C. to about 127° C., and with reactor residence times approximating 60 secs, without the use of a catalyst. It is contemplated, however, that the pyrolysis oil vapor and/or the ethanol can be co-delivered with an acid, or co-delivered across a bed of solid acid catalyst, thereby increasing the yield of the ester product.

It is contemplated that the use of any aliphatic alcohol such as, but not limited to, any primary alcohol like methanol, ethanol, and propanol can be used in the methods and processes of the present disclosure.

Gas chromatography-mass spectroscopy GC-MS results have demonstrated the formation of esters including ethyl acetate and ethyl propionate and acetals including diethoxymethane and 1,1-diethoxyethane. Quantitative GC-MS results indicated that an initial acetic acid concentration can decrease by as much as about 42%, thereby improving the pH (pH was increased from 2.5±0.01 to 3.1±0.01), viscosity (viscosity was reduced from 24.4 to 9.7 cSt (measured at 40° C.)), water content (reduced from 10±0.8 to 8.4±2.3% (w/w)), and cold flow properties of the resultant bio-oil (the cloud point was reduced from −4.7±0.2 to −12.1±0.4° C.) relative to the control.

The ability to reduce the concentration of reactive species in bio-oil provides stable fuel-quality pyrolysis oils derived from biomass. Esterification not only reduces the concentration of the carboxylic acid, e.g. acetic acid; it also improves the overall quality of the bio-oil. Additionally, esters can be easily removed by distillation due to higher volatility compared to the acids from which they are produced. Removed esters are highly valued products in the chemical industry. When left in the bio-oil, esters improve bio-oil quality compared to the carboxylic acids they replace. Esterified bio-oil can be more stable during aging, since acids that would normally catalyze condensation reactions leading to polymerization of bio-oil components are reduced or removed.

It is contemplated that any alcohol may be used to condense and esterify the bio-oil vapor depending on what esters are desired as the end product. For example, but not intended to be limiting, if methanol, butanol, or propanol is used, resulting esters can include methyl, butyl, or propyl acetate, respectively. Additionally, due to the presence of other organic acids in the oils such as, but not limited to, formic acid, propionic acid, and butyric acid, it is possible to produce esters including formates, butyrates, and propionates. The relative size of the esters determines the flash point and boiling point of the bio-oil produced. For example, a bio-oil produced by reactive condensation with methanol will have the lowest flash and boiling points.

One aspect of the present disclosure, therefore, encompasses methods of modifying the content of a pyrolysis oil product, comprising: (a) treating a pyrolysis oil vapor comprising a carbonyl-containing component with an atomized alcohol or amine under conditions allowing a condensation reaction between the carbonyl-containing component and the alcohol or amine, thereby generating a reaction product; and (b) condensing the pyrolysis oil vapor and the reaction product to form a pyrolysis oil product having an increased ester or amide content when compared to a condensed pyrolysis oil product not treated with an atomized alcohol or amine.

In embodiments of this aspect of the methods of the disclosure, the carbonyl-containing component can be selected from the group consisting of: a carboxylic acid species, an aldehyde species, a ketone species, a plurality of carboxylic acid species, a plurality of aldehyde species, a plurality of ketone species, or any combination thereof.

In some embodiments, the carboxylic acid species can have from 1 to 20 carbon atoms, and optionally contain a branched or cyclic structure.

In some embodiments of the methods of the disclosure, the carboxylic acid species can be selected from the group consisting of: formic acid, acetic acid, propionic acid, butyric acid, pentanoic acid, hexanoic acid, heptanoic acid, and octanoic acid, or any branched chain, aromatic, or cyclic derivative thereof.

In embodiments where the pyrolysis oil vapor is treated with an atomized alcohol, the condensation reaction is an esterification, and the reaction product is an ester.

In embodiments where the pyrolysis oil vapor is treated with an atomized amine, the reaction product is an amide.

In some embodiments, the in the condensation reaction can proceed in the absence of a catalyst.

In embodiments of this aspect of the disclosure, the pyrolysis oil product can have an increased stability when compared to a condensed pyrolysis oil product not treated with an atomized alcohol or amine.

In certain embodiments of the methods of the disclosure, the conditions allowing the esterification reaction between the carbonyl-containing component and the alcohol in the absence of a catalyst can comprise a reaction time of about 40 secs to about 70 secs and a temperature of about 110° C. to about 130° C.

In some embodiments of the disclosure, the alcohol can be selected from the group consisting of: an aliphatic alcohol, an unsaturated alcohol, an aryl-substituted aliphatic alcohol, an amino-alcohol, a diol, a triol, a polyol, and any combination thereof.

In some embodiments, the aliphatic alcohol can have from 1 to 20 carbon atoms, and the aliphatic alcohol may be a primary alcohol, a secondary alcohol, or a tertiary alcohol, and optionally may have a branched structure or a cyclic structure.

In embodiments of the methods of the disclosure, the aliphatic alcohol can be selected from the group consisting of methanol, ethanol, 1-propanol, 2-propanol, 2-chloro-1-propanol, 1-chloro-2-propanol, 1-butanol, 2-butanol, isobutanol, tert-butanol, 1-pentanol, 2-methyl-1-butanol, 3-methyl-1-butanol, 2,2-dimethyl-1-propanol, cyclopentanol, 1-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, 3-ethyl-1-butanol, cyclohexanol, 1-octanol, 2-octanol, 2-ethyl-1-hexanol, 1-decanol, 2-decanol, 1-dodecanol, 2-dodecanol, 1-tetradecanol, 2-tetradecanol, 1-hexadecanol, 2-hexadecanol, 1-octadecanol, and 2-octadecanol, and any combination thereof.

In other embodiments of the methods of the disclosure, the alcohol can be a phenolic compound.

In these embodiments, the phenolic compound can have from 1 to 5 condensed aromatic rings.

In some embodiments of the methods of the disclosure, the phenolic compound can be selected from the group consisting of phenol, napthol, 1-hydroxyanthracene, 2-hydroxyanthracene, 1,4-dihydroxyanthracene, 1-hydroxyphenanthrene, 1-hydroxypyrene, hydroxybenzopyrene, hydroxypentacene, hydroxynaphtacene, hydroxychrysene, or a combination thereof.

In other embodiments of this aspect of the disclosure, the amine can be a compound selected from the group consisting of: an alkyl amino, a dialkyl amino, an arylamino, a diarylamino, an alkylarylamino, an alkylaminoaryl, an arylaminoalkyl, an alkaminoalkyl, and any combination thereof.

Another aspect of the disclosure provides a process for generating a pyrolysis oil product, comprising: pyrolyzing a biomass, thereby generating a heated pyrolysis oil vapor comprising at least one carbonyl-containing component; delivering the pyrolysis oil vapor to a reactive condensation unit, delivering an atomized alcohol to the reactive condensation unit, thereby forming a reaction mix comprising the pyrolysis oil vapor and the atomized alcohol or amine; maintaining the reaction mix under conditions suitable for generating at least one condensation reaction product in the absence of a catalyst; and condensing the pyrolysis oil vapor and the at least one condensation reaction product to form a pyrolysis oil product having an increased ester or amide content and increased stability when compared to a condensed pyrolysis oil product not treated with an atomized alcohol or amine.

In embodiments of this aspect of the disclosure, conditions allowing an esterification reaction between the carbonyl-containing component and the alcohol in the absence of a catalyst comprise a reaction time of about 40 secs to about 70 secs and a temperature of about 110° C. to about 130° C.

In some embodiments of this aspect of the disclosure, the process may further comprise delivering a homogeneous acid catalyst to the reactive condensation unit.

In other embodiments, the reactive condensation unit can further comprise a heterogeneous acid catalyst bed.

In embodiments of this aspect of the disclosure, the carbonyl-containing component can be selected from the group consisting of: a carboxylic acid species, an aldehyde species, a ketone species, a plurality of carboxylic acid species, a plurality of aldehyde species, a plurality of ketone species, or any combination thereof.

In some embodiments of this aspect of the disclosure, the carboxylic acid species can have from 1 to 20 carbon atoms, and optionally contains a branched or cyclic structure.

In embodiments of the process of this aspect of the disclosure, the carboxylic acid species can be selected from the group consisting of: formic acid, acetic acid, propionic acid, butyric acid, pentanoic acid, hexanoic acid, heptanoic acid, and octanoic acid, or any branched chain or cyclic derivative thereof.

In embodiments of the process of this aspect of the disclosure, the alcohol can be selected from the group consisting of: an aliphatic alcohol, an unsaturated alcohol, an aryl-substituted aliphatic alcohol, an amino-alcohol, a diol, a triol, a polyol, and any combination thereof.

In embodiments of the process of this aspect of the disclosure, the aliphatic alcohol can have from 1 to 20 carbon atoms, and wherein the aliphatic alcohol is an primary alcohol, a secondary alcohol, or a tertiary alcohol, and optionally has a branched structure or a cyclic structure.

In some embodiments of the process of this aspect of the disclosure, the aliphatic alcohol can be selected from the group consisting of methanol, ethanol, 1-propanol, 2-propanol, 2-chloro-1-propanol, 1-chloro-2-propanol, 1-butanol, 2-butanol, isobutanol, tert-butanol, 1-pentanol, 2-methyl-1-butanol, 3-methyl-1-butanol, 2,2-dimethyl-1-propanol, cyclopentanol, 1-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, 3-ethyl-1-butanol, cyclohexanol, 1-octanol, 2-octanol, 2-ethyl-1-hexanol, 1-decanol, 2-decanol, 1-dodecanol, 2-dodecanol, 1-tetradecanol, 2-tetradecanol, 1-hexadecanol, 2-hexadecanol, 1-octadecanol, and 2-octadecanol, and any combination thereof.

In other embodiments of the process of this aspect of the disclosure, the alcohol can be a phenolic compound.

In embodiments of the process of this aspect of the disclosure, the phenolic compound can have from 1 to 5 condensed aromatic rings.

In embodiments of the process of this aspect of the disclosure, the phenolic compound can be selected from the group consisting of phenol, napthol, 1-hydroxyanthracene, 2-hydroxyanthracene, 1,4-dihydroxyanthracene, 1-hydroxyphenanthrene, 1-hydroxypyrene, hydroxybenzopyrene, hydroxypentacene, hydroxynaphtacene, hydroxychrysene, or combinations thereof.

In other embodiments of the process of this aspect of the disclosure, the amine can be a compound selected from the group consisting of: an alkyl amino, a dialkyl amino, an arylamino, a diarylamino, an alkylarylamino, an alkylaminoaryl, an arylaminoalkyl, an alkaminoalkyl, and any combination thereof.

Yet another aspect of the present disclosure provides a pyrolysis oil product having an decreased carboxylic acid content and increased stability when compared to a pyrolysis oil product not treated with an atomized alcohol or amine according to the processes of the disclosure.

Still yet another aspect of the disclosure provides systems for generating a pyrolysis product, comprising: a pyrolysis unit configured to receive and pyrolyze a biomass, thereby generating a heated pyrolysis oil vapor having a carbonyl-containing component; a reactive condensation unit operably communicating with the pyrolysis unit, wherein the reactive condensation unit is configured to receive the pyrolysis oil vapor and an atomized alcohol or amine, thereby forming a reaction mix within the reactive condensation unit, and further configured to deliver a condensate to a receiving vessel; and a receiving vessel operably disposed to receive a condensate comprising a pyrolysis oil product from the reactive condensing unit.

In embodiments of the process of this aspect of the disclosure, the pyrolysis unit can further comprise a conveyor system disposed within said pyrolysis unit for continual passage of a biomass through the pyrolysis unit.

The specific examples below are to be construed as merely illustrative, and not limiting of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Bio-Oil Production (a) Pyrolysis Reactor

Figure 2:
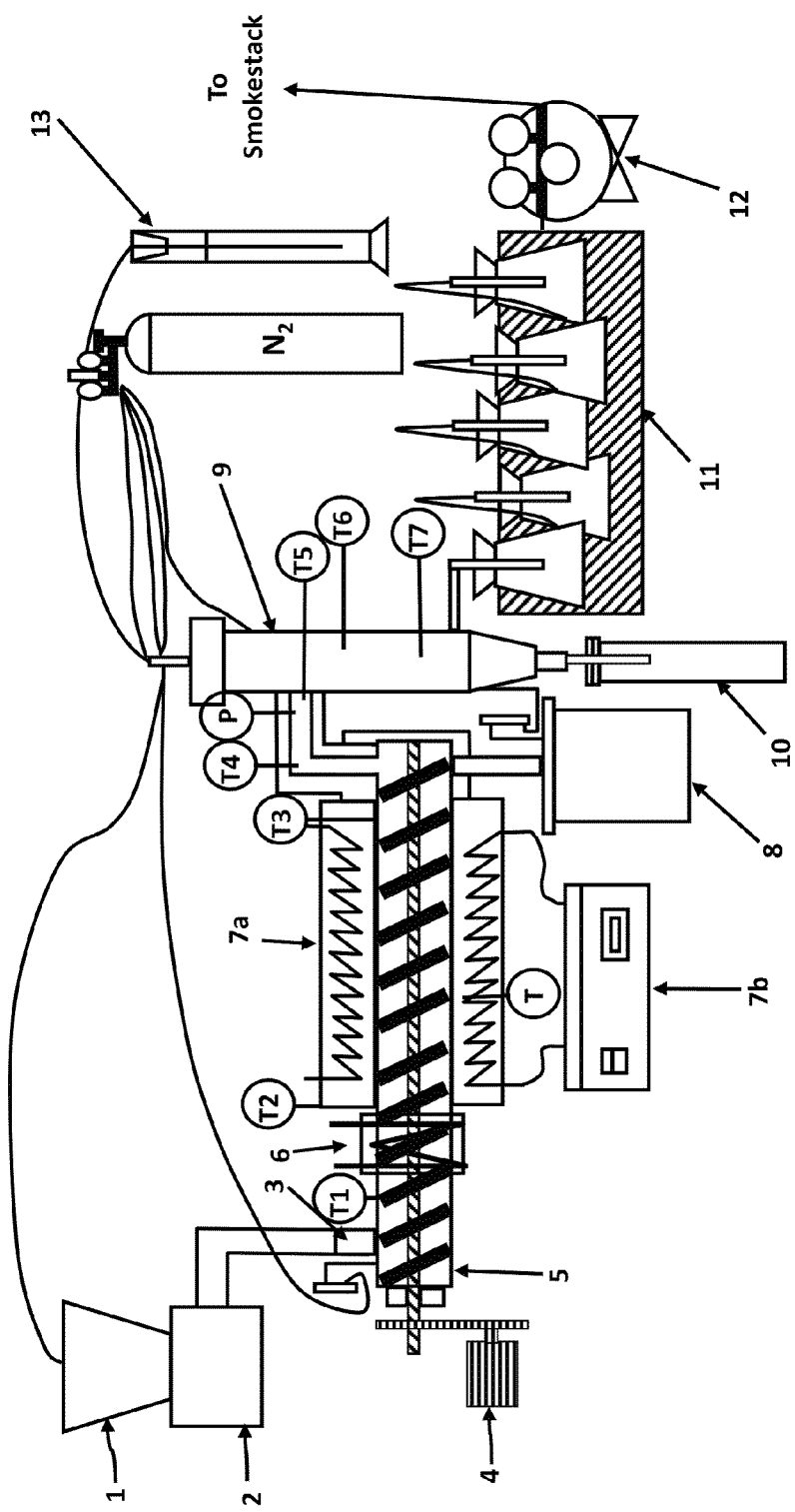
FIG. 2 illustrates a continuous pyrolysis reactor system according to the disclosure including components: (1) biomass hopper, (2) vibratory feeder, (3) reactor inlet, (4) auger motor, (5) auger conveyer, (6) water cooler, (7*a*) furnace and (7*b*) furnace control, (8) char collector, (9) reactive condenser unit, (10) bio-oil receiving vessel (drip trap), (11) ice bath trap, (12) vacuum pump, (13) alcohol container.

FIG. 2 shows the schematic of the transported-bed pyrolysis reactor used in the study. The reactor can consist of, but is not limited to, a 100 mm diameter stainless steel tube containing an auger driven by a ¼ hp electric motor. The auger continuously transported biomass feedstock through the reactor, which was externally-heated by a Lindberg Blue M (model: HTF55322A 1200° C.) furnace. The auger speed was maintained at 1.5 rpm which translated to a solid retention time of 8.26 min in the auger (residence time in the heated zone: 5.91 min).

Biomass feed was supplied to the reactor by an Eriez (Model H036C) vibratory feeder. Feed rate was varied from 0.7 to 3.3 kg h$^{-1}$ in order to vary the weight hourly space velocity (WHSV, dimensionless), the ratio of biomass feed (kg h$^{-1}$) to reactive spray volume (kg h$^{-1}$).

Pyrolysis vapors were directed through a contacting tower (a reactive condenser unit) and a series of five ice-bath traps to condense the bio-oil. To prevent high-boiling vapor (tar) from clogging tubes between the pyrolysis reactor and reactive condenser, the reactor's exhaust line was heated to maintain vapor temperature above 450° C. Non-condensable gases were removed from the system via a vacuum pump attached to the last ice-bath trap in the series. Gases then exited to the atmosphere. Solid material was collected in a stainless steel char collector at the outlet of the reactor where the material was cooled at room temperature under in an inert environment.

An inert atmosphere was maintained in the reactor by supplying nitrogen to various inlets in the system. The nitrogen flow rate was 3 L min$^{-1}$ distributed as follow: 2 L min$^{-1}$ into the main reactor, 0.5 L min$^{-1}$ into the hopper, and 1 L min$^{-1}$ into the char container. Thermocouples, indicated by circled "T" numbers, were installed at various locations to monitor temperatures, as shown in FIG. 2.

(b) Reactive Condensing System

Figure 3:
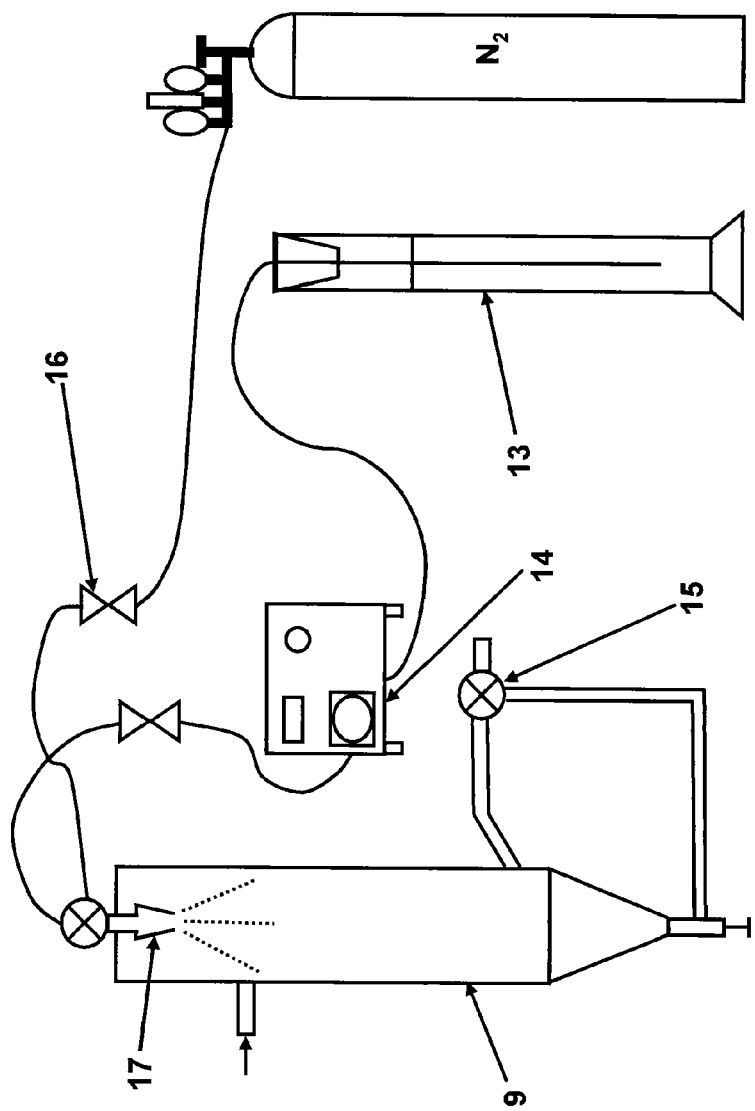
FIG. 3 illustrates a reactive condensing unit for the pyrolysis unit shown in FIG. 1. Items shown figure include; (9) reactive condenser, (14) peristaltic pump, (13) graduated cylinder containing ethyl alcohol, (15) junction, (16) one-way valve, and (17) atomizing nozzle.

FIG. 3 also shows placement of the reactor (component 9 of FIG. 2) used in the experiments to condense and esterify acidic components in the pyrolysis vapor using ethanol. The reactive condensation unit consisted of a 102 mm I.D. stainless steel tube with a reaction zone length, L=457 mm, meaning the reaction zone volume was 3.8 L. In the reactor, vapors were contacted with atomized 100% (200 proof) ethanol ($C_2H_5OH$) that was supplied using a peristaltic pump (Cole-Parmer L/S, model 7524-10) and input to the reactor by a small-bore (0.015 mm diameter) cone-spray atomizer nozzle. In order to achieve adequate atomization of ethanol at low flow rates (1.5-2.0 mL min$^{-1}$), 0.1 L min$^{-1}$ pressurized $N_2$ at 377 kPa (40 psig) was mixed with the ethanol prior to entering the atomizer nozzle. Temperature was measured at the inlet of the reactive condensing unit ("T5") and at two points ("T6" and "T7") along the condenser's length. Heavier liquids condensed in a drip trap directly beneath the reactor. At a carrier gas flow rate of 3.6 L min$^{-1}$, the effective reactor volume (3.8 L) translated to a vapor residence time of 63.3 s in the reaction zone before entering the drip trap. Uncondensed vapor and non-condensable gases were routed through a series of five ice-bath traps that collected the remaining condensable vapor. Non-condensable gases exited to the atmosphere.

(c) Yield of Products

The quantity of biomass in the vibratory feeder hopper was weighed before and after each pyrolysis run to determine the total feed supplied to the reactor. Biomass feed rate was assumed to be steady throughout each run. Solid material, char, was collected and weighed as were condensed liquids in the drip and ice-bath traps. A simple mass balance was used to calculate the quantity of non-condensable gases.

The condensed liquid consisted of two phases, aqueous and oily. After three of the four pyrolysis runs, the drip trap only contained oily phase, while the ice-bath traps contained both oily and aqueous phases. During the fourth run, an oil with two-phases was collected in the drip trap. In all, thirteen samples were produced from four pyrolysis runs. From each of the first three runs at WHSV=13.1-46.3, three samples were produced; a drip oily, an ice-bath oily, and an ice-bath aqueous phase. The fourth run (WHSV=10.3) also produced the additional sample a drip aqueous phase sample. All oils were collected, phase-separated by decantation, quantified and characterized.

Example 2

(a) Biomass and Char

The pine feedstock was supplied in the form of pellets. Moisture, volatiles and ash content in the biomass and chars were determined by ASTM D3 176 using a proximate analyzer (LECO Model TGA70 1). Ultimate analysis (elemental C, H, N, S, and O by difference in wt %) was performed in an ultimate analyzer (LECO Model CHNS-932) following ASTM D5291.

(b) Bio-Oil (Pyrolysis Oil)

Bio-oils produced by the four pyrolysis runs underwent several analyses. Ultimate analysis was performed using the same methods as the biomass. In addition, water content in the oils was determined by Karl Fischer titration using a Mettler-Toledo (Model DL31) titrator following guidelines from ASTM E203. Higher heating value (HHV, in MJ kg$^{-1}$) was assessed using a Parr isoperibol bomb calorimeter (Model 1351) following ASTM D240. Dynamic viscosity, η (in cP), was measured at 25° C. and 45° C. using a Brookfield (Model DV-I+ with UL/YZ spindle adapter) viscometer at three shear rates using a modified version of ASTM D2983. Kinematic viscosity, ν (cSt), was determined by dividing η by specific gravity (SG), which was estimated using a 2 mL Gay-Lussac pycnometer. The pH of the oil was measured directly using a Mettler-Toledo pH meter.

Since only the concentration of ethanol was known in the whole oil, a method was developed using Fourier transform infrared spectroscopy (FT-IR) to determine the quantity of unreacted ethanol in the oily fraction. Samples were analyzed using an FT-IR spectroscope (Varian Scimitar 2000) in attenuated total reflectance (ATR) mode. Ten calibration samples were produced by mixing ethyl alcohol with oily phase bio-oil in known concentrations.

Figure 4:
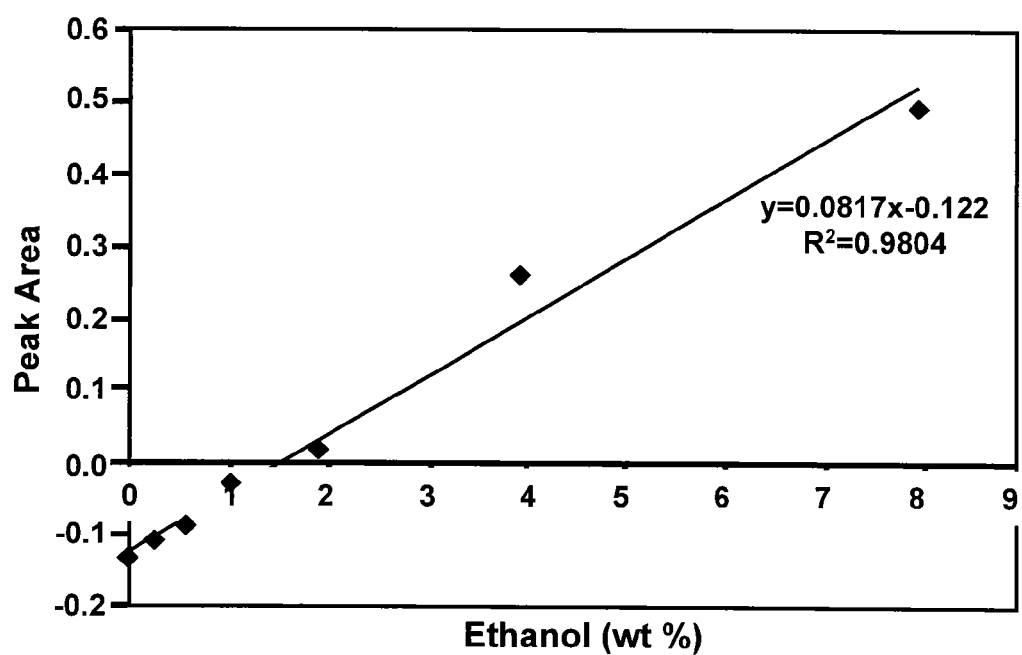
FIG. 4 is a graphical calibration curve for ethyl alcohol/bio-oil mixes based on FTIR absorption spectra peak areas for wave numbers 903-851 $cm^{-1}$.

FIG. 4 shows the calibration curve containing peak areas versus alcohol content for wave numbers 903 cm$^{-1}$ to 851 cm$^{-1}$ that indicate the presence of ethyl alcohol. An FT-IR blank peak produced by bio-oil without ethanol condensing was subtracted from each EtOH/bio-oil mixture.

The formation of esters was verified using a Hewlett-Packard (Model HP-6890) gas chromatograph, containing an HP-5 MS column at 30 m length, 0.25 mm i.d. and 0.25 µm film thickness, in conjunction with a Hewlett-Packard mass spectrometer (Model HP-5973) with a mass selective detector. The method used was as follows: inlet temperature, 230° C., detector temperature, 280° C. (Mass Spec. interface temperature), flow at 1 ml min$^{-1}$ helium, oven at 40° C. for 2.5 min followed by a ramp at 8° C. per min to 250° C. (held for 5 min). Masses were scanned from 15-500 mass units. Sample size was 1 µl and samples were prepared for GC-MS analysis by diluting the bio-oil to 2.5% with acetone.

An internal standard, heptane, was added to each sample-acetone mixture at 0.0625% (v/v). Two model compounds in the bio-oil, acetic acid and ethyl acetate were selected to represent an acid and an ester for quantification. Peak height ratios were calculated for acetic acid and ethyl acetate with the internal standard, heptane. It was assumed that some esters and acids were present in the aqueous phase. No attempts were made to quantify acids and esters in the aqueous phase material. The intent of the work was to improve only the oily phase relative to non-esterified bio-oil.

Chromatograms and spectra were viewed and compounds were identified using Agilent Technologies software (MSD ChemStation D.03.00.611) which uses a probability-based matching (PBM) algorithm to match unknown spectra to those found in a library. The mass spectral library used was the National Institute of Standards and Technology's 1998 version (NIST 98). The quality of a match determined by ChemStation is defined as the probability that the unknown is correctly identified as the reference. The quality can be between 1 and 100 with values above 90 considered very good matches.

A quantification method was developed by producing a five-point standard curve using standard solutions containing mixtures of acetic acid, ethyl acetate, and heptane in acetone. The standard curve yielded a least-squares best-fit line showing the concentration of acetic acid and ethyl acetate versus peak height ratio with heptane. This correlation was then used to predict the concentration of each of the two compounds in the bio-oil samples based on the peak height ratio with heptane calculated for the bio-oils.

Example 3

Carbon and Water Balance

A carbon and water balance was performed upon measuring the carbon, hydrogen sulphur, nitrogen, and water content of the feedstock and all of the pyrolysis products (except non-condensable gases).

Example 4

Bio-Oil Condensing System

Figure 5:
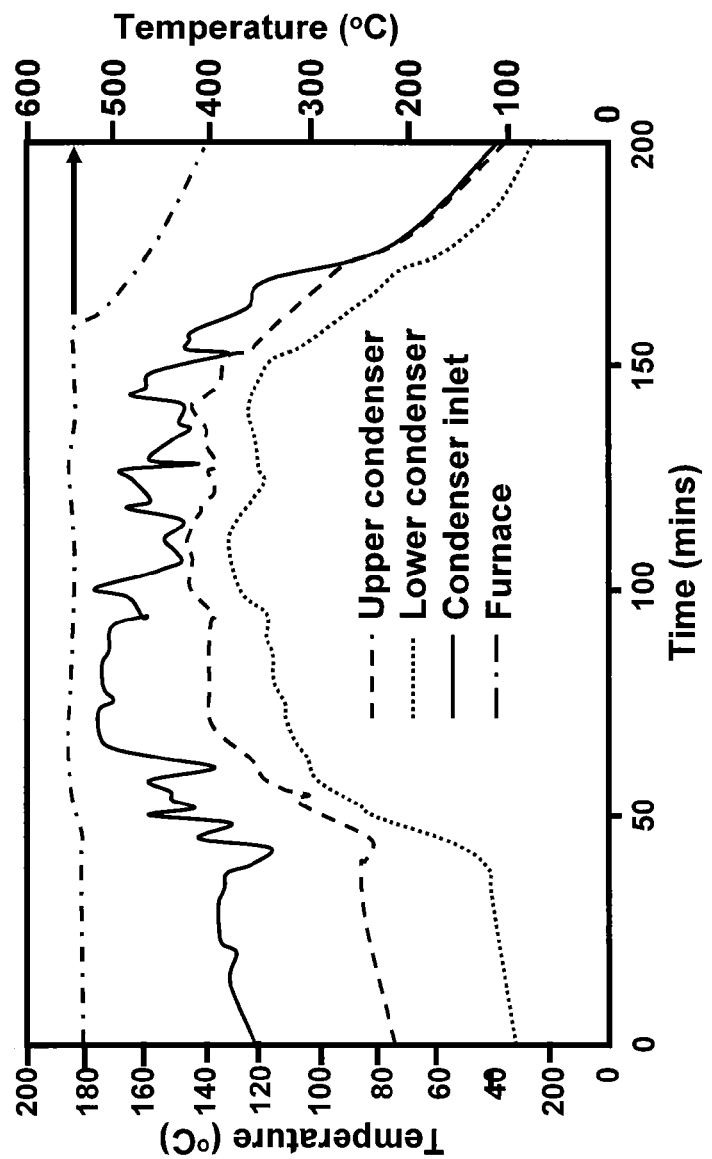
FIG. 5 is a graph showing the temperature profiles obtained during a run producing a bio-oil condensed with 7.4% ethanol (w/w).

The condensing system lowered the bio-oil vapor temperature, such that a liquid formed in the collector below the condenser (drip trap) prior to the ice bath traps. FIG. 5 illustrates temperature profiles obtained during a run producing a bio-oil condensed with 7.4% ethanol (w/w). The start and end times for ethanol atomization during the pyrolysis run shown in FIG. 5 were 60 mins and 150 mins, respectively. The reaction zone was the region between thermocouples T6 and T7 shown in FIG. 2, and it was assumed that the reaction temperature was approximately the average temperature as measured by the two thermocouples.

Despite linearity, the relationship between upper condenser zone temperature and ethanol atomization rate (kg $h^{-1}$) was not statistically significant at $\alpha=0.9$. The relationship between the lower condenser zone temperature (° C.) and ethanol atomization rate was statistically significant at $\alpha=0.05$. The condensation temperature can be controlled by the ethanol and biomass feed rates to selectively condense various bio-oil components. For example, if it is desirable to prevent water from condensing in the receiving vessel, the spray volumes can be adjusted such that the condenser temperature is higher than the condensing temperature of water.

Figure 6:
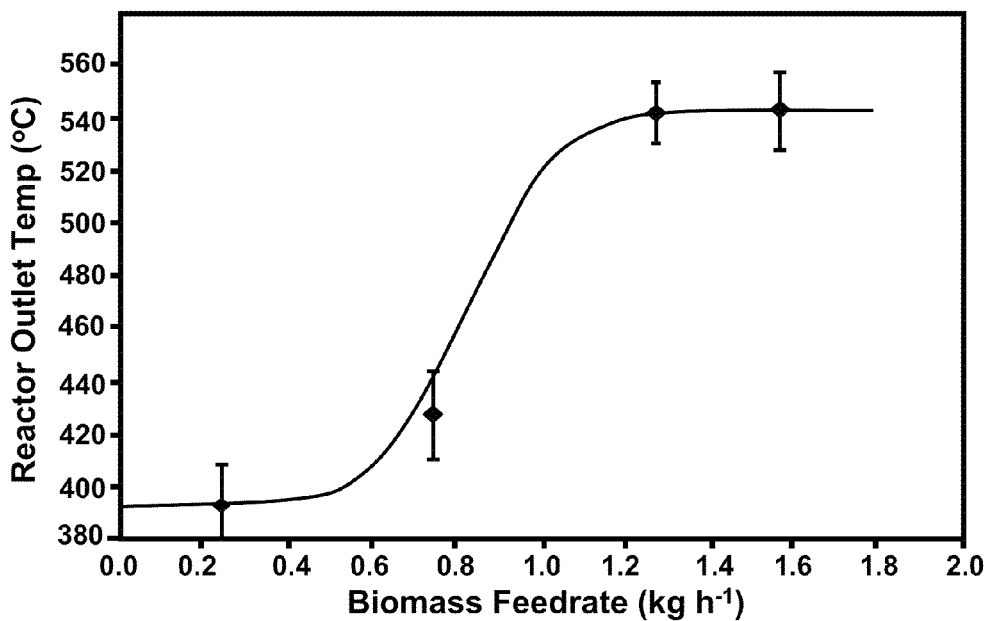
FIG. 6 is a graph showing the effect of biomass feed rate on the temperature of the reactor outlet flow prior to entering the reactive condensing unit.

From FIG. 6, it can be seen that as the biomass feed rate increases, so does the reactor outlet temperature because the pyrolysis vapor and charred solid material have a higher thermal mass than the carrier gas alone. The relationship between feed rate and reactor outlet temperature appears sigmoidal, reaching an asymptote at the furnace temperature on the upper end of the curve.

Figure 7:
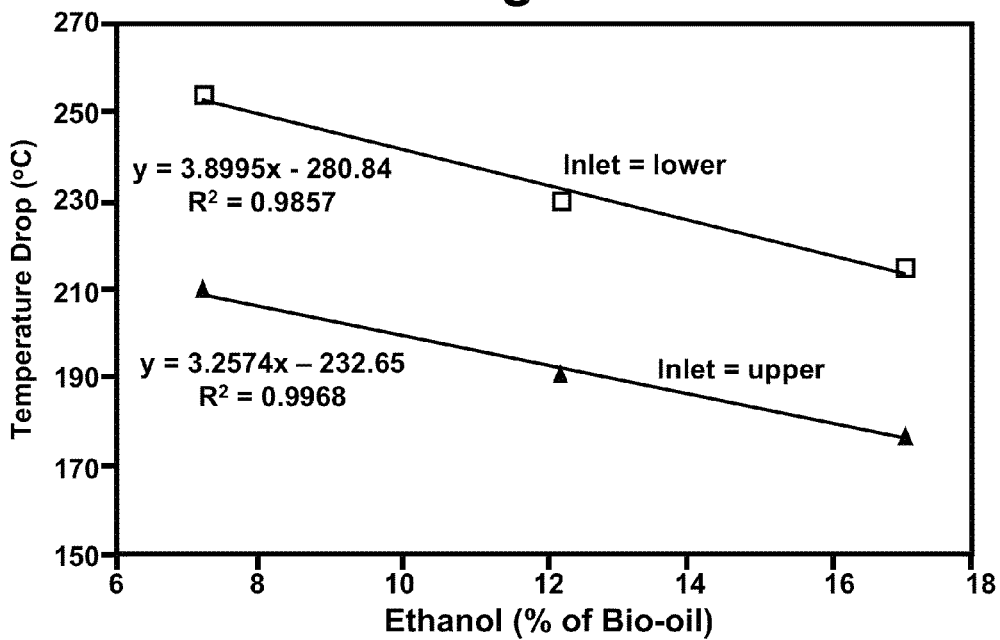
FIG. 7 is a graph illustrating the temperature difference between the condenser inlet and upper portion of condenser (filled triangle) and condenser inlet and lower portion of condenser (open box).

FIG. 7 shows the temperature difference between the condenser inlet and the upper and lower zones in the condensers. The relationship is linear, showing that as the ethanol spray volume increased, the temperature drop decreased. WHSV significantly affected the lower condenser zone temperature at $\alpha=0.1$, but despite linearity, the relationship between WHSV and upper condenser zone temperature was not statistically significant at $\alpha=0.1$. The relationship between lower condenser zone temperature and ethanol spray rate (kg per hr) was statistically significant at $\alpha=0.05$. These correlations are useful, since the condensation temperature can be controlled by the ethanol and biomass feed rate to selectively condense various bio-oil components. For example, if it is desired to prevent water from condensing in the drip trap, spray volume can be adjusted such that the condenser temperature is higher than the condensing temperature of water.

Example 5

Yield of Pyrolysis Products

Table 1 lists the yield of bio-oil components in wt % of original biomass and wt % of total bio-oil at each WHSV.

TABLE 1

Yields for various bio-fuel phases as a function of weighted hourly space velocity or WHSV (kg biomass/kg ethanol)

| Pyrolysis Product | | Wt % Biomass at WHSV | | | | Wt % Total Oil at WHSV | | | |
|---|---|---|---|---|---|---|---|---|---|
| Bio-Oil Drip | | 46.3 | 21.7 | 13.1 | 10.3 | 46.3 | 21.7 | 13.1 | 10.26 |
| | | 52.4 | 59.9 | 53.9 | 47.4 | | | | |
| | Oily | 29.3 | 11.2 | 20.1 | 4.05 | 29.3 | 18.3 | 33.0 | 7.1 |
| | Aqueous | 0.0 | 0.0 | 0.0 | 7.6 | 0.0 | 0.0 | 0.0 | 13.3 |
| Ice-bath | | | | | | | | | |
| | Oily | 34.0 | 6.56 | 4.43 | 9.63 | 34.0 | 10.7 | 7.3 | 16.9 |
| | aqueous | 36.7 | 43.3 | 36.3 | 35.8 | 36.7 | 70.9 | 59.7 | 62.7 |

Figure 8:
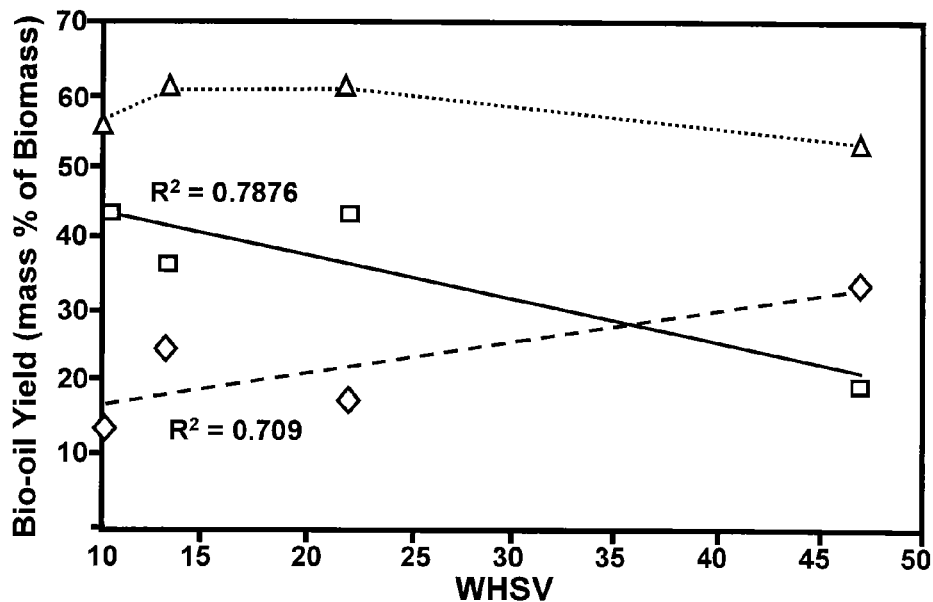
FIG. 8 is a graph illustrating the relationship between the weight hourly space velocity (WHSV) ratio and the yield of oily phase (open diamonds, $R^2=0.71$, p-value>0.05) and aqueous phase (open squares, $R^2=0.79$, p-value>0.05). Solid triangle symbols indicate total bio-oil production.

In runs 1-3, the aqueous phase was not evident in the drip trap. It is evident that with increasing WHSV, the total oily phase yield (wt % of biomass) from both the drip and ice bath traps tends to decrease, while the aqueous phase increases. FIG. 8 shows the relationship between the phase yield and WHSV. Although it appears likely that with increasing WHSV, oily phase increases while aqueous phase decreases, neither relationship is significant at $\alpha=0.05$. The increase in water content of the aqueous phase supports that esterification is occurring, since water is a product of the esterification reaction.

Table 2 lists the yield of bio-oil components as % of original biomass (w/w) and % of total bio-oil (w/w) at each ethanol concentration.

TABLE 2

Product yield for reactive condensation experiments.

| | % Yield (w/w) at % ethanol | | | | |
|---|---|---|---|---|---|
| Product | 0.0 | 7.3 | 10.3 | 16.4 | 23.2 |
| Char | 21.8 | 23.5 | 23.5 | 24.4 | 24.4 |
| Gases[a] | 20.6 | 17.8 | 17.0 | 27.2 | 13.9 |
| Bio-oil Oily Phase | 57.7 | 58.7 | 59.5 | 48.4 | 61.7 |
| (% of BO[b]) | 17.5 | 21.6 | 17.1 | 19.2 | 9.0 |
| (% of BM[c]) | 9.0 | 11.6 | 9.6 | 9.5 | 6.0 |
| Aqueous Phase | | | | | |
| (% of BO) | 82.5 | 78.4 | 82.9 | 80.8 | 91.0 |
| (% of BM) | 42.4 | 42.0 | 36.5 | 40.0 | 40.4 |

[a]Calculated by difference;
[b]Bio-oil;
[c]Biomass.

Figure 9:
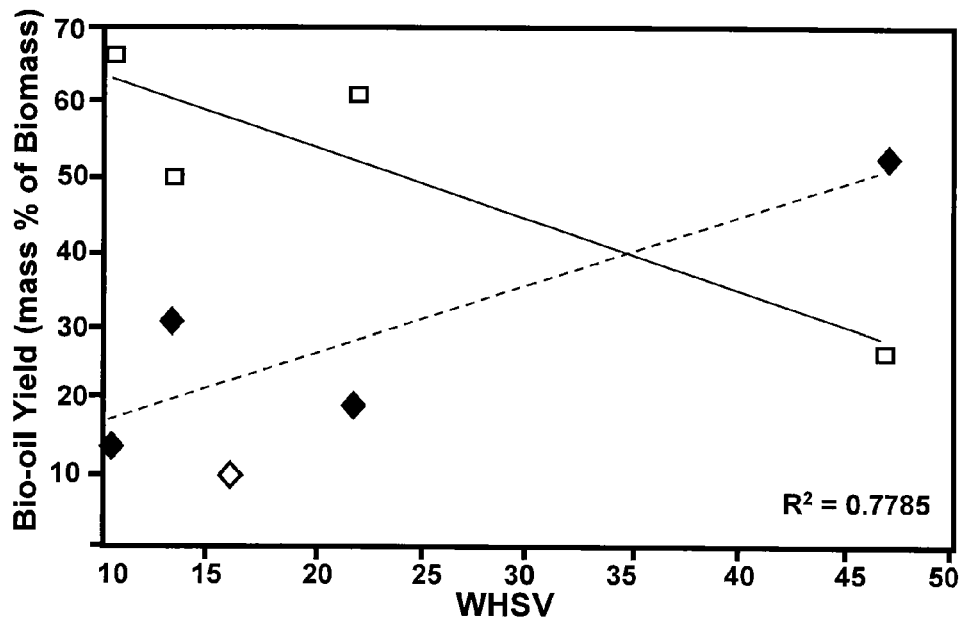
FIG. 9 is a graph illustrating the yield of oily (open squares) and aqueous (closed diamonds) phase at WHSV. Best-fit lines for oily phase (solid line, $R^2=0.78$, p-value>0.05) and aqueous phase (dashed line, $R^2=0.78$, p-value>0.05) yield are shown.

The yield of un-condensed gas was calculated by difference such that the mass balance inevitably added to 100%. From FIG. 9 it is evident that with increasing WHSV, the total oily phase yield (% of biomass, w/w) decreases while aqueous phase increases. Although it appeared that with increasing WHSV the oily phase increased and the aqueous phase decreased, neither relationship was significant at $\alpha=0.05$. However, the apparent increase in aqueous phase with concurrent decrease in water content in the oily phase relative to non-esterified bio-oil supports the hypothesis that esterification occurred.

The pyrolysis run with the lowest WHSV (10.3 or 17 wt % ethanol, Table 1; 8.3 or 26.2 wt % ethanol, Table 2;) produced a two-phase oil in the drip trap, although an oily phase material also condensed in the ice bath traps. Aqueous phase yield in the drip trap indicated that the temperature in the reactive condenser was below the boiling point of at least some of the aqueous phase components. Also, the increase in the yield of aqueous phase shown in FIGS. 8 and 9 indicated that a water-generating reaction, such as esterification, had occurred.

Example 6

Characterization of Materials (a) Biomass and Char: Table 3 shows the characterization of the pine pellet biomass (PP BM) and pine pellet char (PP CH) produced during continuous pyrolysis at 500° C.

TABLE 3

Characterization of solid feedstock and pyrolysis char

| Analysis[a] | Biomass | Char |
|---|---|---|
| Moisture (w.b.) | 7.45 | 3.20 |
| Volatiles | 74.83 | 27.58 |
| Ash | 0.13 | 2.7 |
| Fixed carbon | 17.59 | 69.12 |
| C | 52.6 | 79.1 |
| H | 5.66 | 3.1 |
| N | 0.18 | 0.2 |
| S | 0.02 | 0.0 |
| O[b] | 38.9 | 12.6 |
| HHV (MJ/kg) | 20.6 | 34.1 |

[a]Measured as a wt % (d.b.) unless otherwise stated;
[b]By difference

These data were used to determine water and carbon balances for the system.
(b) Bio-oil: Table 4 shows characterization data for the bio-oil for each of the four runs as well as for ethanol.

TABLE 4

Characterization data for oily-phase bio-oils produced at various WHSV

| | Oily Phase Characteristics at WHSV | | | | |
|---|---|---|---|---|---|
| Parameter | 46.3 | 21.7 | 13.1 | 10.26 | ethanol |
| ethanol (wt %) | | | | | |
| Ultimate Analysis | | | | | |
| C | 55.0 | 51.2 | 48.9 | 62.1 | 46.6 |
| H | 6.22 | 7.05 | 5.64 | 6.49 | 11.7 |
| N | 0.09 | 0.11 | 0.10 | 1.37 | 0.0 |
| S | 0.03 | 0.04 | 0.04 | 0.03 | 0.0 |
| O* | 38.7 | 41.6 | 45.3 | 30.0 | 41.7 |
| HHV (MJ/kg) | 18.6 | 19.4 | 21.3 | 26.6 | 27.2 |
| % H$_2$O | 20.7 | 13.6 | 9.66 | 5.68 | 0.43 |
| pH | 1.87 | 1.80 | 1.96 | 1.82 | 5.29 |

TABLE 4-continued

Characterization data for oily-phase bio-oils produced at various WHSV

| | Oily Phase Characteristics at WHSV | | | | |
|---|---|---|---|---|---|
| Parameter | 46.3 | 21.7 | 13.1 | 10.26 | ethanol |
| Viscosity (cSt) | | | | | |
| 25° C. | 27.9 | 216 | 45.65 | 209 | 3.75 |
| 45° C. | 33.7 | | | 341 | 3.99 |
| Density (g/mL) | 1.21 | 1.16 | 1.14 | 1.13 | 0.80 |

It is clear from Table 4 that oily phase water content increased with increasing WHSV (decreased ethanol spray). Additionally with a higher concentration of ethanol spray, oxygen content in the oil decreased, though the relationship is not linear. A decrease in oxygen content is desirable especially if the bio-oils are to be used as fuels, since oxygen content decreases heating value. A reduction in elemental oxygen is consistent with formation of esters. If carboxylic acids react with ethanol to form esters as hypothesized, the oxygen content should decrease. In the reaction of acetic acid (53.3 wt % oxygen, theoretical) with ethanol (34.8 wt % oxygen, theoretical), ethyl acetate is formed with an oxygen content of 36.4 wt %. The oxygen from acetic acid is concentrated in the reaction by-product, water, and should be concentrated in the aqueous phase of the condensed product.

Figure 10:
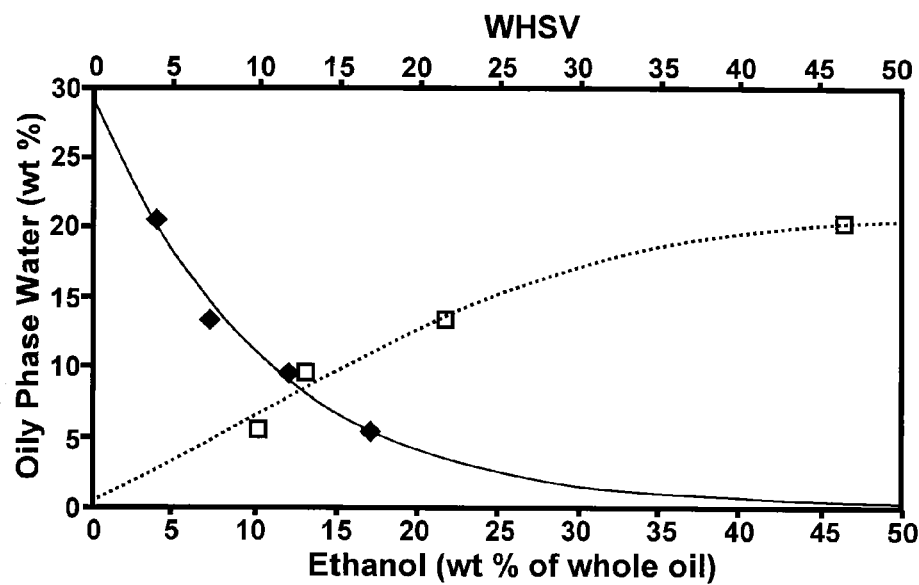
FIG. 10 is a graph illustrating the oily phase water content as a function of ethanol (solid diamonds) and WHSV (open squares). Logistic best-fit lines for ethanol (solid line, $R^2=0.99$, p-value<0.01) and WHSV (dashed line, $R^2=0.99$, p-value<0.01) are shown.

FIG. 10 provides an indication of the relationship between ethanol (wt % of whole oil) and water content of the oily phase. It is proposed that the relationship, at least in the range of interest, is best fit by a logistic regression line. However, it is expected that the trend will continue as wt % ethanol is increased resulting in a horizontal asymptote for the lower leg of the best-fit line approaching the water content of the ethanol (~0 wt % H$_2$O). This result is also consistent with the formation of esters. With greater ethanol volume sprayed, a greater concentration of esters in the bio-oil is expected. Since esters are less polar than the organic acids from which they were formed, water is less soluble in the bio-oil. Decreased solubility of water in the bio-oil means that water content in the oily phase will decrease while water content in the aqueous phase increases.

Lower biomass feed to ethanol spray ratios tend to lower the water content significantly. However, at an undetermined threshold WHSV (denoted as the single-phase threshold) between 3.8 and 8.2, the bio-oil produced exists as a single phase with high water content. This was observed during a previous experiment that produced two single-phase bio-oils with WHSV at 1.5 and 4.8 (57 wt % ethanol and 28 wt % ethanol) with water content at 11.5 wt % and 26.2 wt %, respectively. Since the ethanol and water content of the whole oil is known for these samples, and the water content for ethanol is known, the water content of only the bio-oil can be calculated. For WHSV at 1.2 and 3.8, water content was calculated to be 20.1 wt % and 34.4%, respectively. However, it is obvious that decreasing the WHSV still reduces water content in bio-oils even below the single phase threshold, though more experimentation is needed to determine that threshold and the extent of water content reduction.

Table 5 also shows the high heating value (HHV in MJ kg$^{-1}$) of the bio-oils produced including those of the ethanol alone and the single-phase oils produced in an earlier experiment.

TABLE 5

Ethyl alcohol content in the oily phased of bio-oil as determined by FT-IR analysis using the calibration curve as shown in FIG. 4.

| Ethanol (wt % in whole oil) | Absorbance Peak Area | Predicted ethanol (wt % in oily phase) |
|---|---|---|
| 0.0 | −0.17 | −0.53 |
| 3.9 | 0.33 | 5.53 |
| 7.2 | 0.35 | 5.77 |
| 12.2 | 0.49 | 7.51 |
| 16.8 | 0.20 | 3.99 |

Figure 11:
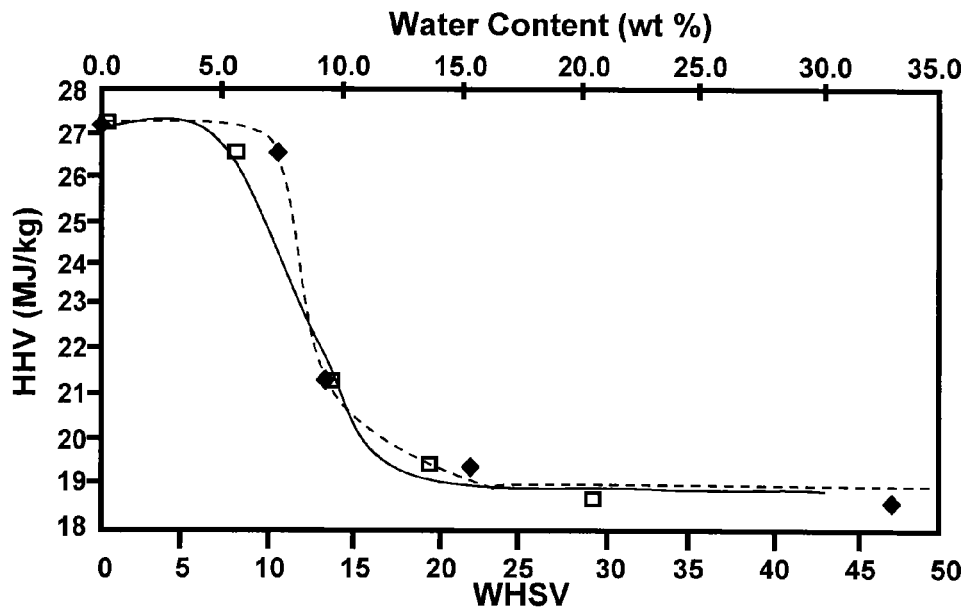
FIG. 11 is a graph illustrating the higher heating value (HHV) versus WHSV (closed diamonds) and $H_2O$ content (open squares). Dotted and solid lines show logistic regression best-fit curve for WHSV ($R^2=0.996$, p-value<<0.01) and $H_2O$ content ($R^2=0.997$, p-value<<0.01), respectively.

HHV in the bio-oil increases with increasing ethanol feed rate. The sample produced at WHSV 10.4 (17 wt % ethanol) showed similar HHV to ethanol. However, as indicated by both FT-IR and GC-MS, very little unreacted ethanol is present in the bio-oil. Since esters, especially ethyl acetate (HHV=25 MJ kg$^{-1}$), are formed in relatively high concentration, it is expected that the increase in heating value is due to their presence as opposed to ethanol. Additionally with decreasing water content, HHV should increase. In FIG. 11, logistic regression best-fit lines showing the relationship between both HHV and water content and HHV and WHSV exhibit sigmoidal-type behavior. The upper leg approaches an asymptote at the HHV of the proposed esters while the lower leg approaches the heating value of bio-oil without esterification at the lower asymptote. With an R$^2$=0.996 (p-value<<0.01) and R$^2$=0.997 (p-value<<0.01), it is apparent that the relationship between HHV and WHSV and HHV and water content are significant at $\alpha$=0.01.

Kinematic viscosity, ν, shows an interesting but inconsistent phenomenon in Table 3. That is, viscosity increases as more ethanol is added to the whole oil. This indicates that the lower viscosity ethanol is not necessarily incorporated into the oily phase of the bio-oil. This is verified by data in Table 4 that show ethanol content in the oily phase as determined by FT-IR. Additionally, the lower water content in the oily phase at lower WHSV likely contributes to higher viscosity. The phenomenon of an inconsistent trend in viscosity was not evident when samples from drip and ice-bath traps were combined, as in Example 7, below, and as shown in Table 8.

Figure 12:
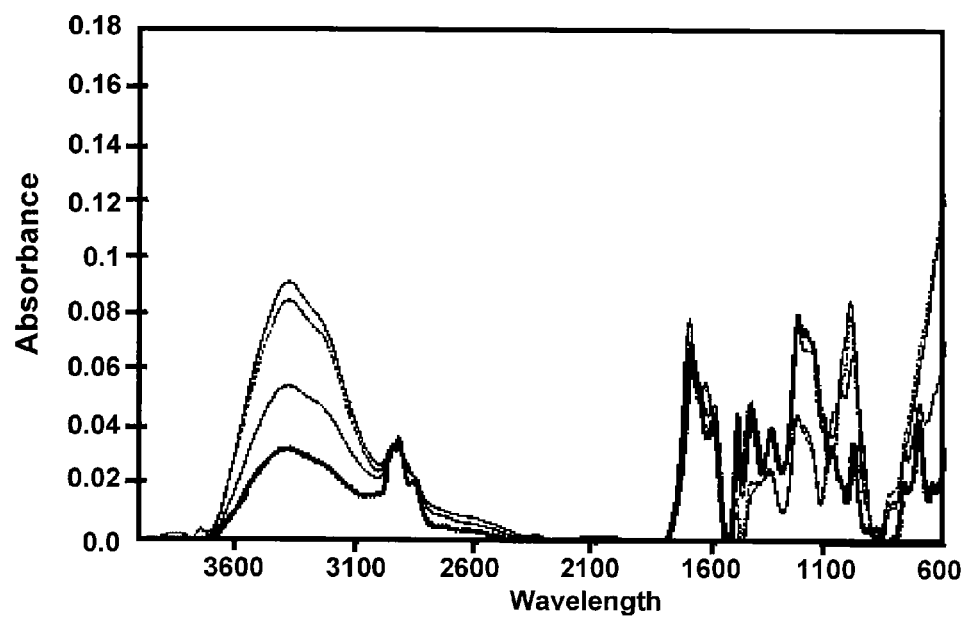
FIG. 12 is a graphical representation of the FT-IR spectra for bio-oils condensed using ethanol. Spectra show results for 0.0 (thick grey dotted line), 3.9 (light dotted line), 7.2 (solid line), 12 (short dashed line), and 17 wt % ethanol (long dashed line) of whole bio-oil.

FIG. 12 shows FT-IR spectra for four ethanol sprayed samples (WHSV at 10.3, 13.1, 21.7, and 46.3) and for a bio-oil with no spray. It is apparent that bio-oil without ethanol added has lower absorbance in the range from 3700 to 2500, a region representing O—H stretching vibrations consistent with the presence of ethyl alcohol. The trend in this region is unclear for the alcohol-condensed bio-oils. However, the spectra indicate that at least some portion of ethanol remains unreacted in the condensed bio-oil.

Table 6 and 7 lists the peak areas and retention times for ethyl acetate and other compounds in the bio-oil samples along with the quality points of the match (0-100).

TABLE 6

GC/MS results for ethyl acetate formation in the esterified bio-oil

| ethanol | | | Ethyl Acetate | | |
|---|---|---|---|---|---|
| Wt % | WHSV | RT | Peak Ht | Peak Area | Quality |
| 0 | ∞ | — | 0 | 0 | — |
| 3.9 | 46.3 | 2.13 | 12200000 | 243084341 | 70 |
| 7.2 | 21.7 | 2.07 | 25000000 | 404998706 | 68 |
| 12.2 | 13.1 | 2.15 | 27000000 | 456129668 | 64 |
| 17 | 10.3 | 2.05 | 27500000 | 457000000 | 87 |

Quality: MS spectral match with a NIST database—value of 100 would be a perfect match;
WHSV: weighted hourly space velocity; kg biomass/kg of ethanol;
RT: retention time of the ethyl acetate peak in minutes

TABLE 7

Effect of ethanol on bio-oil composition based on GC/MS analysis and percent peak area

| | | % Ethanol | | | | |
|---|---|---|---|---|---|---|
| Compound | Quality | 0.0 | 7.3 | 10.3 | 16.4 | 23.2 |
| | | % Peak Area | | | | |
| Acetic Acid | 50-52 | 1.79 | 2.02 | 1.65 | 3.86 | ND |
| Ethyl Acetate | 58-90 | 0 | 0.20 | 0.28 | ND | 4.01 |
| 1-hydroxy-2-propanone | 72-80 | 1.66 | 2.70 | 2.72 | 6.2 | 5.68 |
| Furfural | 87-91 | 3.22 | 2.66 | 3.14 | 7.02 | 6.2 |
| 2-mthoxy-Phenol | 95-97 | 4.42 | 4.3 | 5.22 | 4.46 | 3.54 |
| 2-methoxy-4-methyl-phenol | 95 | 9.93 | 11.42 | 12.48 | 5.73 | 8.45 |
| 4-ethyl-2-methoxy-phenol | 91 | 6.5 | 7.11 | 8058 | 3.83 | 5.84 |
| 2-methoxy-4-(1-propenyl)-phenol | 97 | 8.5 | 10.78 | 11.73 | 4.7 | 10.36 |
| n-hexadecanoic acid | 95-99 | 2.34 | 0.56 | 0.51 | ND | ND |

Figure 13:
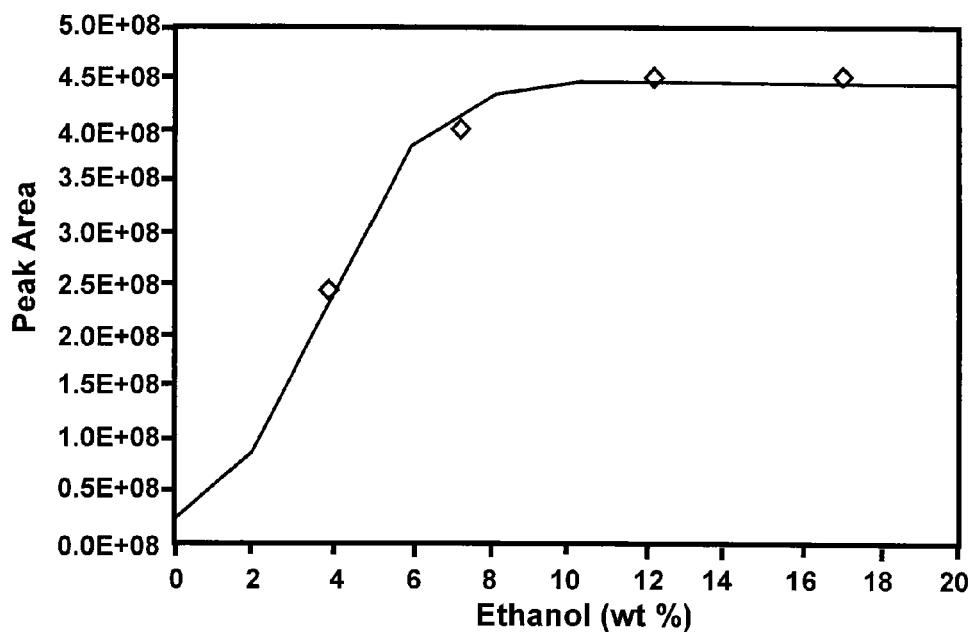
FIG. 13 is a graph showing the peak areas for ethyl acetate for bio-oils produced with ethanol content at 0, 3.9, 7.2, 12.2, and 17 (wt % of whole oil). The dotted line shows the logistic best-fit line ($R^2=0.996$).

ND—not detected
WHSV: ratio of biomass feed rate to ethanol feed rate, kg biomass/kg ethanol
Quality: Match compared to a MS NIST database with 100 representing a perfect match FIG. 13 shows peak area of ethyl acetate obtained from gas chromatograph spectra versus ethanol (wt % of whole oil) and figures in the appendix demonstration the formation of ethyl acetate. It is apparent that as more ethanol is added, ethyl acetate production increases until some asymptote is reached, at which point, maximum conversion of acetic acid to ethyl acetate has been attained. The limitation is likely the result of amount of acetic acid available in the bio-oil that is required for the ethyl acetate-forming reaction. Since the reaction is reversible, it will reach some equilibrium between products and reactants. However, since water is condensed downstream and not with the bio-oil, the reaction favors the product, ethyl acetate, with little potential for the reverse reaction between ethyl acetate and water to reform ethanol and acetic acid.

Gas chromatograph-mass spectrograph (GC-MS) spectra for each of the esterified bio-oils (23.2% ethanol), for the control sample, and for ethyl acetate and acetic acid reference materials were obtained by dissolving the sample in acetone at 2.5 wt % except for ethyl acetate and acetic acid reference samples that were dissolved at 1.6 and 1.0%, respectively. The GCIMS chromatograms demonstrated an esterification reaction between ethanol and acids in the bio-oil (primarily acetic acid). The peak for acetic acid is reduced and subsequently a peak for ethyl acetate is formed. Other acids in the bio-oil disappear, but we were not able if identify additional unknown peak that subsequently formed in the reacted bio-oil. It is also clear that many methoxylated phenols are formed but don't react in the esterification step (Table 6).

Example 7

Product Characterization bio-oil, or that other reactions such as acetylations could generate higher oxygen content products.

Results further indicated that as the ethanol % w/w was increased, the water content in the oily phase decreased. Table 8 provides water content values for oil collected and combined from both receiving vessel (drip trap) and ice bath traps. Here too, the water content decreased with increasing ethanol, although the relationship was not significant, at $\alpha=0.05$. The results were consistent with the formation of a more non-polar bio-oil and esters.

With greater ethanol volume sprayed, a greater concentration of esters in the bio-oil was expected. Since esters are less polar than the organic acids from which they are formed, water solubility in the resultant bio-oil would be expected to decline. Decreased water solubility in the bio-oil will decrease the water content in the oily phase and increase the water content in the aqueous phase.

Although lower biomass feed to ethanol spray ratios (i.e., WHSV) lowered the water content at an undetermined threshold WHSV (denoted as the single-phase threshold) between 3.8 and 8.2, the bio-oil produced existed as a single phase with

TABLE 8

Characterization data for oily-phase bio-oils produced at various WHSV.

| | Oily Phase Characteristics at WHSV | | | | | |
|---|---|---|---|---|---|---|
| | ∞ | 33.3 | 25 | 16.7 | 8.3 | 0 |
| Parameter | | | | | | |
| ethanol (wt %) | 0 | 7.4 | 10.3 | 16.4 | 23.2 | 100 |
| C | $64.9 \pm 1.7^b$ | $57.9 \pm 2.0$ | $56 \pm 0.5$ | $56.6 \pm 0.4$ | $55.8 \pm 1.4$ | $46.6 \pm 3.4$ |
| H | $7.1 \pm 0.4$ | $5.6 \pm 0.6$ | $5.6 \pm 0.4$ | $6.4 \pm 0.1$ | $6 \pm 0.1$ | $11.7 \pm 0.7$ |
| N | $0.2 \pm 0.03$ | $0.2 \pm 0.01$ | $0.3 \pm 0.02$ | $0.2 \pm 0.02$ | $0.2 \pm 0.03$ | $0 \pm 0.01$ |
| S | $0 \pm 0.02$ | $0 \pm 0.01$ | $0 \pm 0.01$ | $0 \pm 0.00$ | $0 \pm 0.01$ | $0 \pm 0.01$ |
| $O^a$ | $27.8 \pm 1.4$ | $36.3 \pm 1.9$ | $38.1 \pm 0.5$ | $36.7 \pm 0.4$ | $38 \pm 1.6$ | $41.7 \pm 0.00$ |
| HHV (MJ kg$^{-1}$) | $27.6 \pm 0.2$ | $24.5 \pm 0.1$ | $25.7 \pm 0.6$ | $25.2 \pm 0.05$ | $27 \pm 0.2$ | $27.2 \pm 3.8$ |
| % H$_2$O | $10 \pm 0.8$ | $16.2 \pm 2.6$ | $11.2 \pm 0.2$ | $14 \pm 0.9$ | $8.4 \pm 2.3$ | $0.4 \pm 0.01$ |
| pH | $2.48 \pm 0.01$ | $2.65 \pm 0.02$ | $2.74 \pm 0.03$ | $2.82 \pm 0.02$ | $3.05 \pm 0.01$ | $5.29 \pm 0.4$ |
| Viscosity (mm$^2$ s$^{-1}$) | | | | | | |
| 40° C. | 300.1 | 151.2 | 41.3 | 37.2 | 49.2 | $3.75^c$ |
| 60° C. | 24.4 | 13.7 | 13.5 | 11.2 | 9.7 | 3.99 |
| Density (g mL$^{-1}$) | $1.18 \pm 0.2$ | $1.19 \pm 0.2$ | $1.15 \pm 0.1$ | $1.11 \pm 0.2$ | $1.06 \pm 0.1$ | $0.8 \pm 0.01$ |

$^a$By difference;
$^b$"±XX.X" indicates ± one standard deviation;
$^c$Ethanol viscosity as measured at 25° C. and 45° C.

Analysis of results for the oily phase untreated with ethanol are also shown. Results from Table 8 show that the oily phase water content generally decreases with higher ethanol atomization rate, although the relationship is not statistically significant. In addition, as evidenced by the ultimate analysis of the oils, elemental oxygen content appeared to increase with increasing ethanol. A reduction in elemental oxygen would be consistent with formation of esters assuming that no ethanol remained unreacted in the product. If carboxylic acids react with ethanol to form esters, the oxygen content will decrease.

In the reaction of one mole of acetic acid at 53.3% w/w oxygen with one mole of ethanol at 34.8% w/w oxygen, one mole of ethyl acetate is formed with an oxygen content of 36.4% w/w, which is lower than that of acetic acid. Some of the oxygen from acetic acid is concentrated in the reaction by-product, water, and will partition in the aqueous phase of the condensed product, thereby increasing the aqueous phase yield, as seen in FIG. 13 with the decreasing WHSV. Since oxygen concentration does not decrease with increasing ethanol, it is likely that some ethanol remained unreacted in the high water content. This was also observed during a previous experiment in which two single-phase bio-oils were generated with WHSV at 1.5 and 4.8 (57% w/w and 28% w/w ethanol) with water content at 11.5 and 26.2 wt %, respectively. For the oily phase samples of this study, the water content was reduced by as much as 16%. Previous studies witnessed greater reductions. However, their starting material of fast pyrolysis oil had a water content at 33% compared to the 10% for the control bio-oil of the present experiments. Nonetheless, there was no increase in water content achieved through reactive condensation.

Table 8 also shows high heating value (HHV in MJ kg$^{-1}$) for the bio-oils generated. HHV in the bio-oil increases with increasing ethanol feed rate. The sample produced at WHSV 8.3 (23.2 wt % ethanol) showed similar HHV to ethanol. Since esters, particularly ethyl acetate (HHV=25 MJ kg$^{-1}$), are formed in relatively high concentrations (1.89 to 3.42 μL mL$^{-1}$), it was anticipated that the increase in heating value was partially due to their presence. Additionally, with decreasing water content, HHV should increase. For bio-oil collected from all traps (receiving vessel and ice-traps), HHV ranged from 24.5 to 27.6 MJ kg$^{-1}$ indicating little change in HHV due to esterification. It has been shown that HHV increases as large as 52% (from 16 MJ kg$^{-1}$ to 24 MJ kg$^{-1}$) when using fast pyrolysis oil as the esterification reactant. Since the starting pyrolysis oil material of the present studies, the slow pyrolysis bio-oil, already had a relatively high HHV at 27 MJ kg$^{-1}$ compared to fast pyrolysis oils (16 MJ kg$^{-1}$) and esters (about 25 MJ kg$^{-1}$), an increase due to esterification was not clearly evident.

Figure 14:
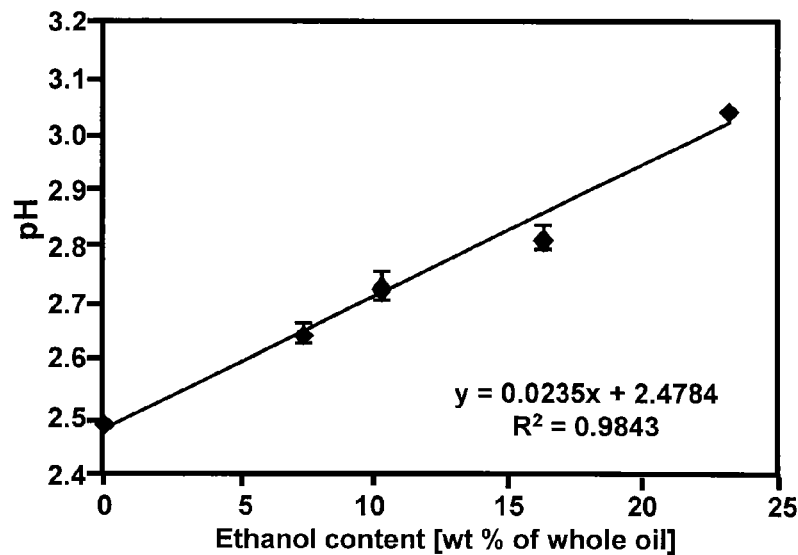
FIG. 14 is a graph illustrating the relationship between pH and ethanol % (w/w).

Another indication of the esterification reaction is the increase in pH with increasing ethanol % w/w, as shown in FIG. 14. As acids such as acetic acid are consumed in the reaction with ethanol resulting in ester production, the overall acidity of the bio-oil was reduced. The relationship between pH and ethanol % is significant at α=0.05.

Example 8

Viscosity

Figure 15:
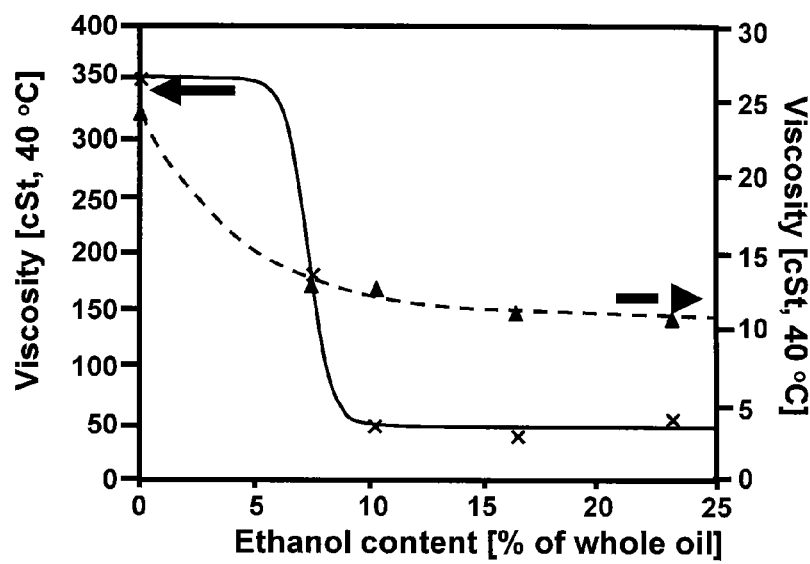
FIG. 15 is a graph illustrating the viscosity at 40° C. and at 60° C. as a function of ethanol fitted with a 5-parameter sigmoidal line at $R^2=0.999$ and $R^2=0.996$ (p<0.05), respectively.

It is desirable to lower viscosity bio-oil such that it is similar to values specified for No. 2 diesel fuel (1.9-4.1 mm$^2$ s$^{-1}$) by ASTM D975, "Standard Specification for Diesel Fuel Oils." Kinematic viscosity values, v, of the bio-oils produced by the processes of the present disclosure are shown in Table 8. The viscosity decreased substantially as more ethanol was added to the reactive condensation unit relative to the oil component, as shown in FIG. 15, showing a non-linear decrease in viscosity at 40° C. and 60° C. as a function of ethanol concentration.

Although water content in the oily phase is lower at lower WHSV, which generally results in higher viscosity, the opposite was the case with the esterified oils. Using fast pyrolysis bio-oil as the reactant, Zhang et al., ((2006) *Energy Fuels* 20: 2717-2720) saw a decrease in viscosity from 49 to 4.9 mm$^2$ s$^{-1}$ when measured at 20° C. after the bio-oil was esterified with ethanol. The reductions seen with the bio-oil products of the present disclosure were similar using slow pyrolysis bio-oil as the reactant, with a reduction from 300 to as low as 37 mm$^2$ s$^{-1}$ when measured at 40° C. In contrast, Moens et al., ((2009) *Energy Fuels* 23: 2695-2699) performed acid-catalyzed bio-oil esterifications while removing water by azeotropic distillation. Although there was significant decreases in acidity (as measured by total acid number), the resulting oil was a semi-solid tar with poor flow characteristics.

Example 9

Table 9 shows cloud point (both in ° C.) for the reactively-condensed bio-oils.

TABLE 9

Oxidation onset and cloud point temperatures for ethanol-condensed bio-oils.

| Ethanol | Cloud Point [° C.] | |
|---|---|---|
| [wt %] | Ave | S.D. |
| 0 | −4.7 | 0.2 |
| 7.4 | −7.3 | 0.4 |
| 10.3 | −7.9 | 0.3 |
| 16.4 | −6.7 | 1.0 |
| 23.2 | −12.1 | 0.3 |

One measure of stability is the resistance to polymerization as evidenced by a viscosity increase. Junming et al., ((2008) *Biomass Bioenergy* 32: 1056-1061) showed that after three months of aging, esterified bio-oil exhibited very little viscosity increase. Despite the lack of evidence for an increase in stability in the current study, cold flow properties were improved as evidenced by the linear decrease in cloud point as WHSV decreases (ethanol increases-Table 4). A linear regression best-fit line showed an $R^2$=0.79 and a p-value<0.05. Thus, the relationship between cloud point and ethanol content is significant at α=0.05.

Example 10

Figure 16:
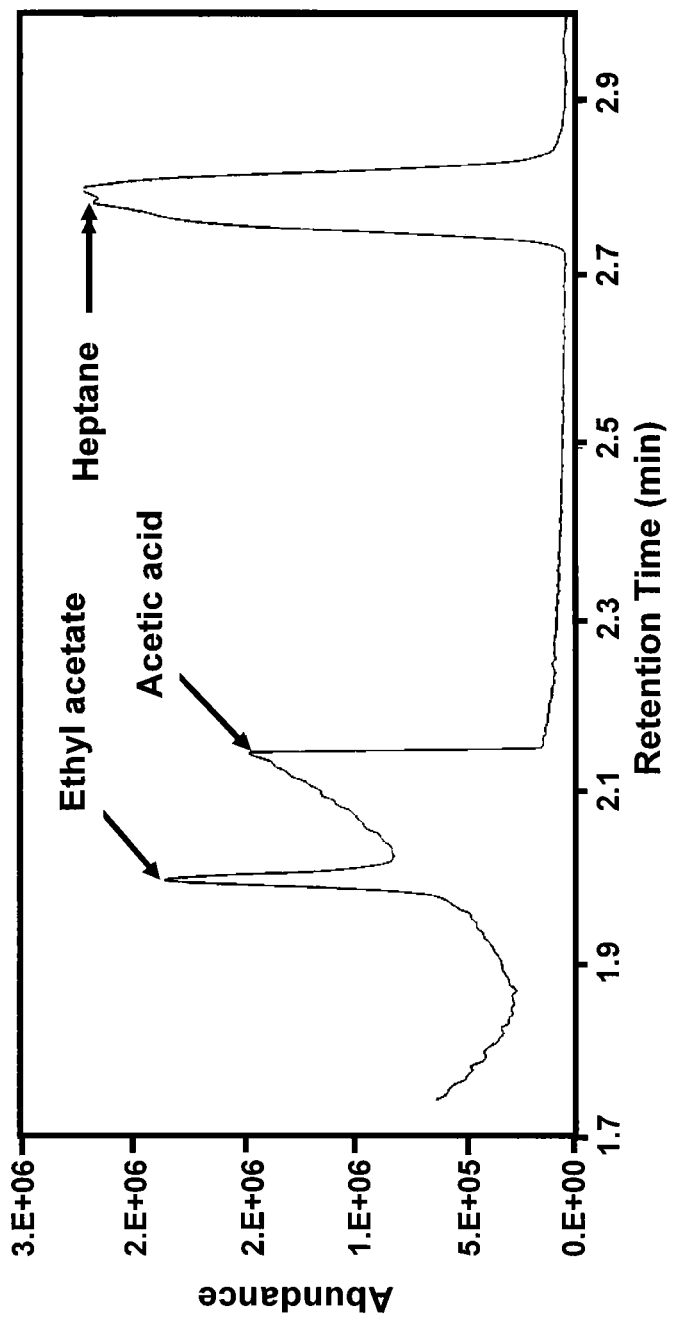
FIG. 16 illustrates the gas chromatogram for calibration standard containing ethyl acetate (retention time=1.999, quality: 72), acetic acid (retention time=2.142, quality: 90), and heptane (retention time=2.8, quality: 90).

FIG. 16 shows the chromatogram for one of the calibration samples in which the ethyl acetate, acetic acid, and heptane peaks were clearly evident at retention times of 1.99, 2.05, and 2.8 min, respectively. For five calibration standards, peak height ratios for acetic acid and ethanol with heptane were determined and used to calculate concentration in experimental samples. Ethanol likely reacts with other carboxylic acids in the bio-oil (e.g., formic, propionic, butyric acid), with aldehydes (e.g., acetaldehyde, formaldehyde, propionaldehyde, furfural) and with ketones (e.g., acetone, propanone, butanone), forming multiple products. However, only the effects of ethanol addition on the yield of ethyl acetate are quantified here.

Example 11

Figure 17:
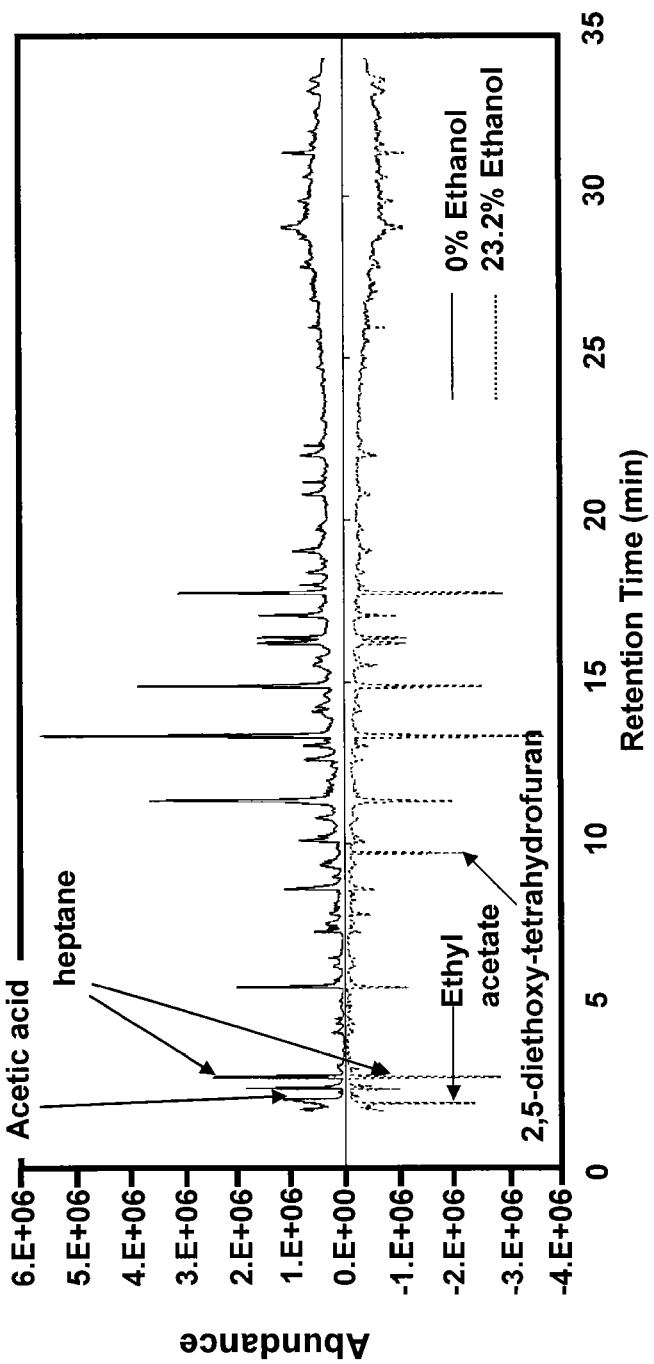
FIG. 17 illustrates the gas chromatogram for bio-oil samples with 0 and 23.2% (w/w) ethanol including internal standard, heptane (retention time=2.798 min), showing ethyl acetate (retention time=1.996) and acetic acid (retention time=2.046) peaks.

FIG. 17 shows the chromatograms for the control sample and for the 23.2% ethanol sample from retention times at 2 min to 34 min. The two chromatograms are substantially similar but several key differences are clear. First, a large peak at 9.7 min in the 23.2% sample identified as 2,5-diethoxytetrahydrofuran (quality: 91) does not appear in the control. This compound was likely formed as product of several reactions stemming from the interaction between ethanol and furfural, an aldehyde. Furfural is visible at 5.6 min (quality>90) in both spectra but with lower abundance in the esterified bio-oil indicating that the concentration of furfural has been reduced.

Figure 18:
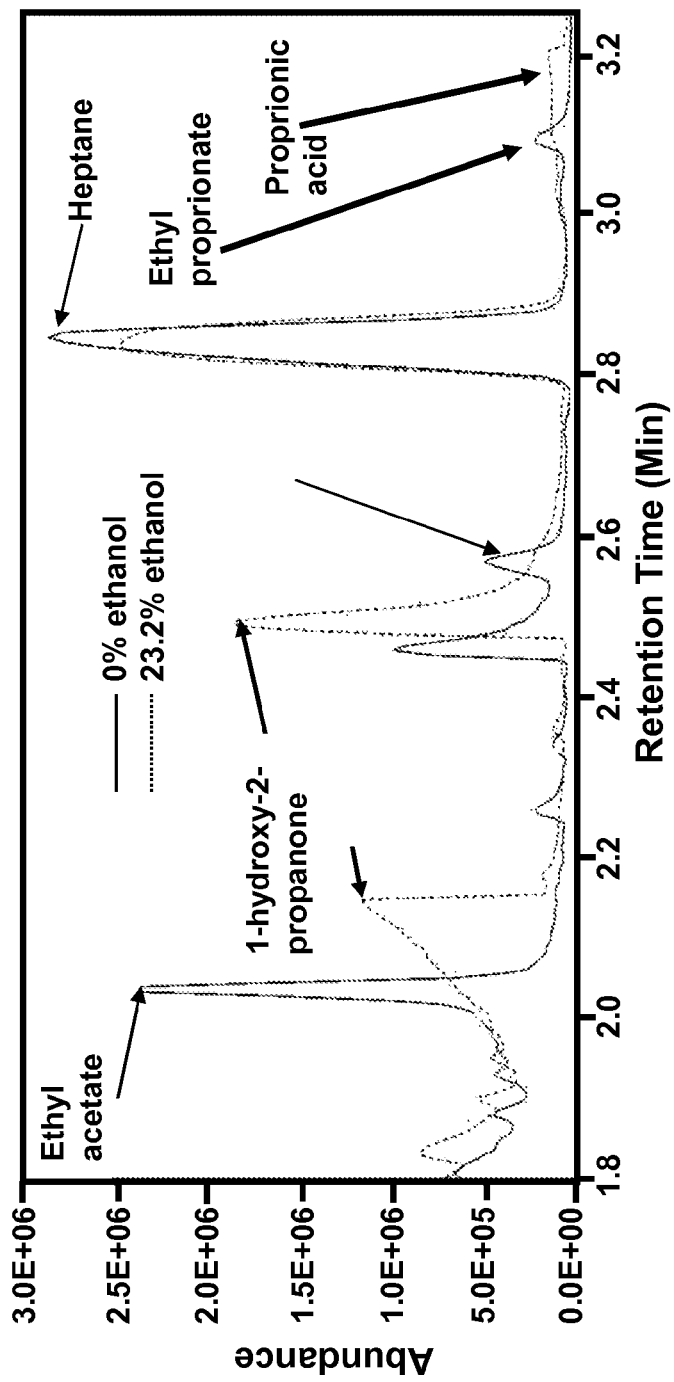
FIG. 18 illustrates the gas chromatogram for 0% (w/w) and 23.2% (w/w) ethanol bio-oil samples showing ethyl acetate (quality: 72), acetic acid (quality: 90), heptane (quality: 94 and 90, respectively) and various other compounds.
Figure 19:
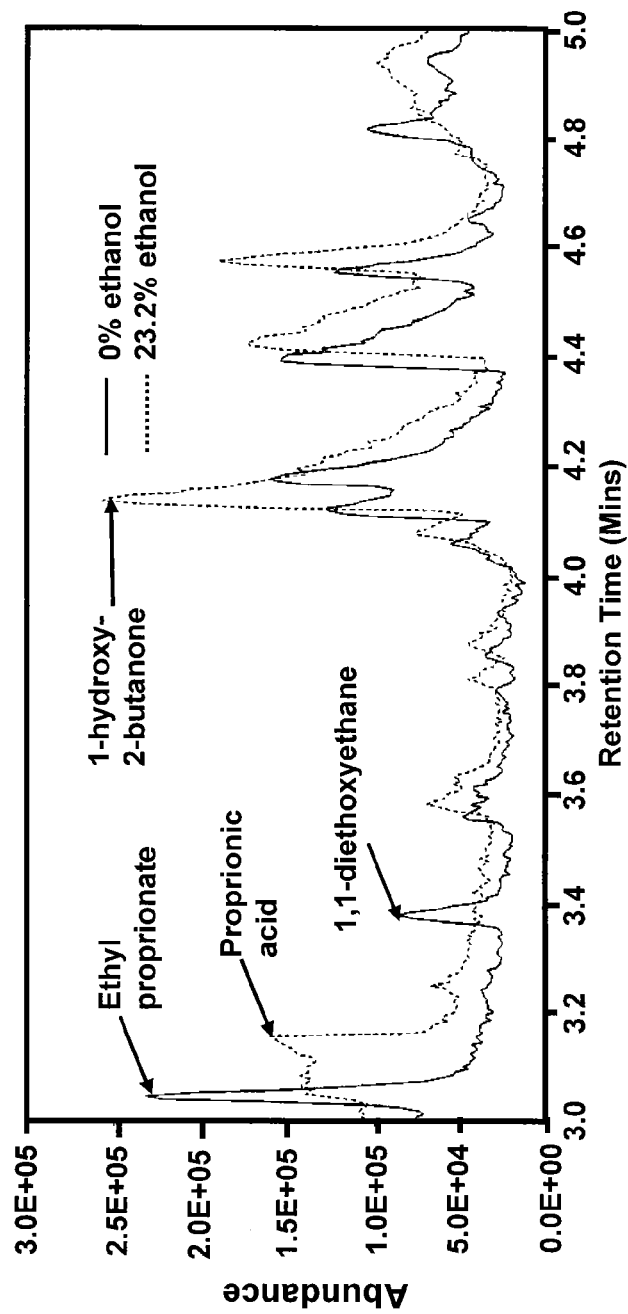
FIG. 19 illustrates the gas chromatogram for bio-oil condensed with 0 and 23.2% (w/w) ethanol.

Though not quantified, acetals, products of the reaction between ethanol and aldehydes, were identified in the chromatograms. Two acetalization products were identified by the ChemStation software; thus, in FIG. 18, diethoxymethane (2.58 min), and in FIG. 19, 1,1-diethoxyethane (3.34 min), were identified in the spectrum of the 23.2% ethanol sample, but not in the 0% ethanol sample. Diethoxymethane and 1,1-diethoxyethane are likely the products of ethanol reacting with formaldehyde and acetaldehyde, respectively.

However, ChemStation was not able to identify either formaldehyde or acetaldehyde in the bio-oil samples. This may be a limitation of the GC column used. An additional esterification reaction, that of propionic acid with ethanol, was indicated by the presence of propionic acid in the 0% ethanol sample, but not in the 23.2% sample for which ethyl propionate, an ester, is evident.

Example 12

Figure 20:
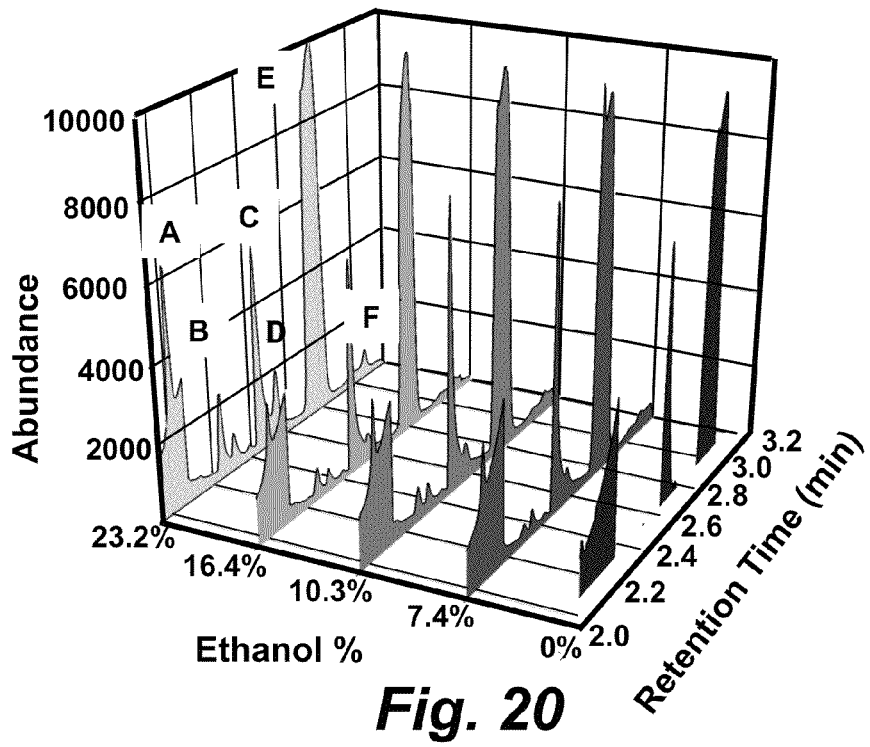
FIG. 20 illustrates a stacked plot showing normalized gas chromatograms for each ethanol concentration. Compounds include ethyl acetate (A), acetic acid (B), 1-hydroxy-2-propanone (C), diethoxymethane (D), heptane (E), and ethyl propionate (F).

FIG. 20 shows exemplary chromatograms for a series of ethanol concentrations. It is clear that acetic acid (peak B) decreases with ethanol concentration increases, thereby producing a concurrent increase in ethyl acetate abundance (peak A). Peak C, 1-hydroxy-2-propanone appears to decrease relative to the internal standard, indicating a reduction in concentration. Also seen in FIG. 20, the small peak (F) indicates the concentration of ethyl propionate increases with increasing ethanol concentration.

Example 13

Figure 21:
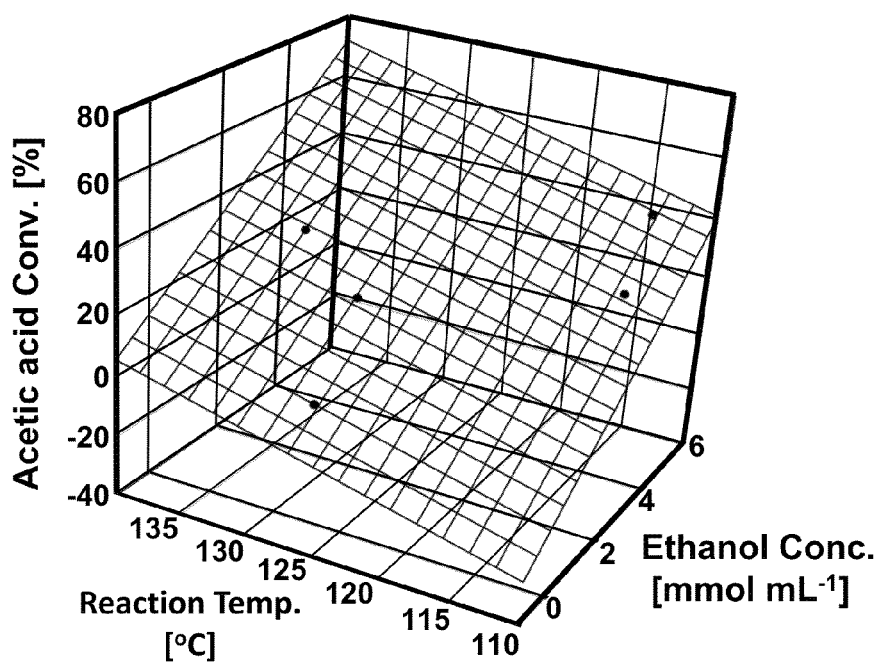
FIG. 21 is a graph illustrating the fractional conversion of acetic acid (AA) as a function of reaction temperature [° C.] and ethanol concentration [mmol $mL^{-1}$] ($R^2=0.996$, p<0.01).
Figure 22:
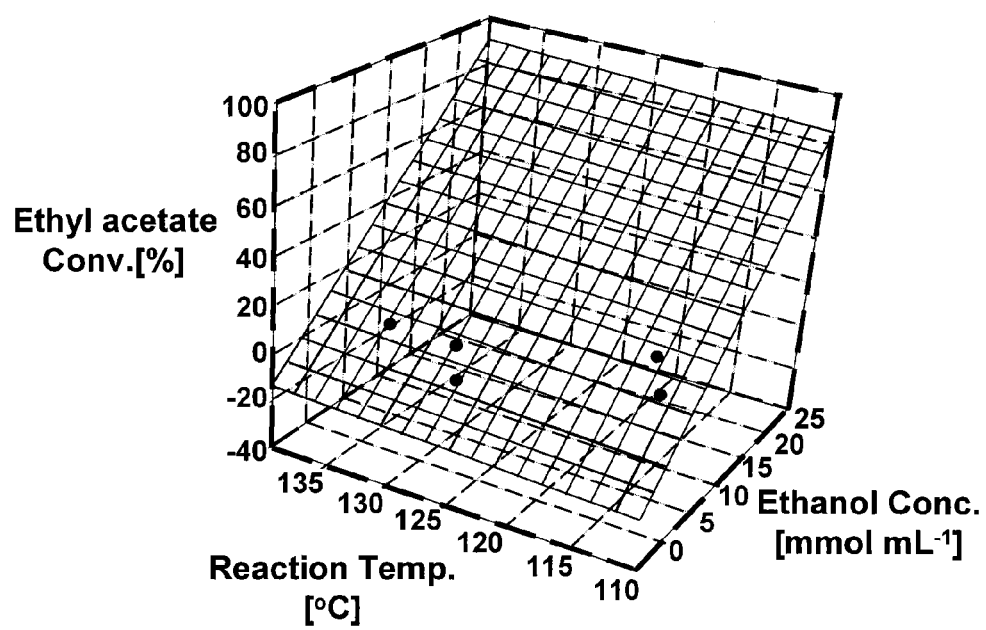
FIG. 22 is a graph illustrating the fractional conversion of acetic acid to ethyl acetate (EA) as a function of reaction temperature [° C.] and ethanol concentration [mmol $mL^{-1}$] ($R^2=0.89$, p<0.1).

The yield results from the calibrated GC-MS methods are shown in FIGS. 21 and 22. Fractional conversion of acetic acid in % (v/v) shown in FIG. 21 was calculated as the change in concentration (in mmol mL$^{-1}$) divided by the concentration of acetic acid (mmol mL$^{-1}$) in the control sample for which no ethanol was added during condensation. Both reaction temperature and ethanol concentration relative to the whole oil significantly affect (at $\alpha=0.05$) the conversion of acetic acid.

FIG. 22 shows the fractional yield (%, v/v) of ethyl acetate assuming that the expected yield is equivalent to the fractional conversion of acetic acid. The concentration of ethanol is a significant predictor of ethyl acetate fractional conversion at $\alpha=0.9$ while the reaction temperature is not. It is assumed that losses of ethyl acetate during storage and transfer of bio-oil due to high volatility of ethyl acetate account for some of the variability in fractional conversion. The highest yield of ethyl acetate (19%) was at 23.2% ethanol, which compares well with other studies. For example, Koster et al., ((2001) J. Catal. 204: 333-338) observed ethyl acetate yields that were at most 25% when using a catalyst and long reaction times (>250 min). The method of the disclosure generated esters without a catalyst at reaction times of approximately 60 s.

From FIGS. 21 and 22 it is apparent that the esterification reaction is a function of temperature and reactant concentration, since the conversion of acetic acid increased with reaction temperature (FIG. 21) and as more ethanol was added, acetic acid conversion (ethyl acetate formation) increased (FIG. 22). Ultimately, the reaction will be limited by the amount of reactants in the bio-oil vapor available for esterification. Since the reaction is reversible, it will reach equilibrium between products and reactants. The removal of water shifts the equilibrium towards products. Equilibria for esterification reactions lies far to the right, especially if conducted in vapor phase. The thermodynamic equilibrium constant is 367 for the reaction of ethanol and acetic acid to form ethyl acetate. Because the reaction is carried out in the vapor phase, water vapor and bio-oil vapor containing reactants (e.g., acids, aldehydes, ketones) are spatially separated so water in the reaction medium affects reaction equilibria less than it would in liquid phase reactions. Thus, for the observed esterification reaction between acetic acid and ethanol, the reaction strongly favors the product, ethyl acetate, with little potential for the reverse reaction between ethyl acetate and water to reform ethanol and acetic acid.

We claim:

1. A method of modifying the content of a pyrolysis oil product, comprising:
    (a) treating a pyrolysis oil vapor comprising a carbonyl-containing component with an atomized alcohol or amine under conditions allowing a condensation reaction between the carbonyl-containing component and the alcohol or amine, wherein the conditions allowing the condensation reaction between the carbonyl-containing component and the alcohol in the absence of a catalyst comprise a reaction time of about 40 secs to about 70 secs and a temperature of about 110° C. to about 130° C., thereby generating a reaction product; and
    (b) condensing the pyrolysis oil vapor and the reaction product to form a pyrolysis oil product having an increased ester or amide content when compared to a condensed pyrolysis oil product not treated with an atomized alcohol or amine.

2. The method according to claim 1, wherein the carbonyl-containing component is at least one of a carboxylic acid species, an aldehyde species, a ketone species, or any combination thereof.

3. The method according to claim 2, wherein the carboxylic acid species has from 1 to 20 carbon atoms, and optionally contains a branched or cyclic structure.

4. The method according to claim 2, wherein the carboxylic acid species is formic acid, acetic acid, propionic acid, butyric acid, pentanoic acid, hexanoic acid, heptanoic acid, or octanoic acid, or any branched chain, aromatic, or cyclic derivative thereof.

5. The method according to claim 1, wherein the condensation reaction proceeds in the absence of a catalyst.

6. The method according to claim 1, wherein the alcohol is at least one of an aliphatic alcohol, an unsaturated alcohol, an aryl-substituted aliphatic alcohol, an amino-alcohol, a diol, a triol, or a polyol, or any combination thereof.

7. The method according to claim 6, wherein the aliphatic alcohol has from 1 to 20 carbon atoms.

8. The method according to claim 6, wherein the aliphatic alcohol is at least one of methanol, ethanol, 1-propanol, 2-propanol, 2-chloro-1-propanol, 1-chloro-2-propanol, 1-butanol, 2-butanol, isobutanol, tert-butanol, 1-pentanol, 2-methyl-1-butanol, 3-methyl-1-butanol, 2,2-dimethyl-1-propanol, cyclopentanol, 1-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, 3-ethyl-1-butanol, cyclohexanol, 1-octanol, 2-octanol, 2-ethyl-1-hexanol, 1-decanol, 2-decanol, 1-dodecanol, 2-dodecanol, 1-tetradecanol, 2-tetradecanol, 1-hexadecanol, 2-hexadecanol, 1-octadecanol, and 2-octadecanol.

9. The method of claim 1, wherein the amine is at least one of an alkyl amino, a dialkyl amino, an arylamino, a diarylamino, an alkylarylamino, an alkylaminoaryl, an arylaminoalkyl, and an alkaminoalkyl.

10. A method of modifying the content of a pyrolysis oil product, comprising:
    (a) treating a pyrolysis oil vapor comprising a carbonyl-containing component with an atomized amine under conditions allowing a condensation reaction between the carbonyl-containing component and the amine, thereby generating an amide; and
    (b) condensing the pyrolysis oil vapor and the amide to form a pyrolysis oil product having an increased amide content when compared to a condensed pyrolysis oil product not treated with an atomized amine.

11. A method of modifying the content of a pyrolysis oil product, comprising:
    (a) treating a pyrolysis oil vapor comprising a carbonyl-containing component with an atomized alcohol under conditions allowing a condensation reaction between the carbonyl-containing component and the alcohol, wherein the pyrolysis oil vapor is treated with an atomized alcohol and the condensation reaction is an esterification reaction, thereby generating an ester reaction product, and wherein the conditions allowing the esterification reaction between the carbonyl-containing component and the alcohol in the absence of a catalyst comprise a reaction time of about 40 secs to about 70 secs and a temperature of about 110° C. to about 130° C.; and
    (b) condensing the pyrolysis oil vapor and the condensation reaction product to form a pyrolysis oil product having an increased ester content when compared to a condensed pyrolysis oil product not treated with an atomized alcohol.

12. A method of modifying the content of a pyrolysis oil product, comprising:
   (a) treating a pyrolysis oil vapor comprising a carbonyl-containing component with an atomized alcohol under conditions allowing a condensation reaction between the carbonyl-containing component and the alcohol, thereby generating a reaction product, wherein the alcohol is a phenolic compound; and
   (b) condensing the pyrolysis oil vapor and the reaction product to form a pyrolysis oil product having an increased ester content when compared to a condensed pyrolysis oil product not treated with an atomized alcohol.

13. The method according to claim 12, wherein the phenolic compound has from 1 to 5 condensed aromatic rings.

14. The method of claim 12, wherein the phenolic compound is at least one of phenol, napthol, 1-hydroxyanthracene, 2-hydroxyanthracene, 1,4-dihydroxyanthracene, 1-hydroxyphenanthrene, 1-hydroxypyrene, hydroxybenzopyrene, hydroxypentacene, hydroxynaphtacene, and hydroxychrysene.

15. A process for generating a pyrolysis oil product, comprising:
   pyrolyzing a biomass, thereby generating a heated pyrolysis oil vapor comprising at least one carbonyl-containing component;
   delivering the pyrolysis oil vapor to a reactive condensation unit,
   delivering an atomized alcohol to the reactive condensation unit, thereby forming a reaction mix comprising the pyrolysis oil vapor and the atomized alcohol;
   maintaining the reaction mix under conditions suitable for generating at least one condensation reaction product in the absence of a catalyst, wherein the conditions allowing an esterification reaction between the carbonyl-containing component and the alcohol in the absence of a catalyst comprise a reaction time of about 40 secs to about 70 secs and a temperature of about 110° C. to about 130° C.; and
   condensing the pyrolysis oil vapor and the at least one condensation reaction product to form a pyrolysis oil product having an increased ester content and increased stability when compared to a condensed pyrolysis oil product not treated with an atomized alcohol.

16. The method according to claim 15, wherein the carbonyl-containing component is at least one of a carboxylic acid species, an aldehyde species, and a ketone species.

17. The method according to claim 16, wherein the carboxylic acid species has from 1 to 20 carbon atoms, and optionally contains a branched or cyclic structure.

18. The method according to claim 16, wherein the carboxylic acid species formic acid, acetic acid, propionic acid, butyric acid, pentanoic acid, hexanoic acid, heptanoic acid, or octanoic acid, or any branched chain or cyclic derivative thereof.

19. The process according to claim 15, wherein the alcohol is at least one of an aliphatic alcohol, an unsaturated alcohol, an aryl-substituted aliphatic alcohol, an amino-alcohol, a diol, a triol, and a polyol.

20. The process according to claim 19, wherein the aliphatic alcohol has from 1 to 20 carbon atoms, and wherein the aliphatic alcohol is an primary alcohol, a secondary alcohol, or a tertiary alcohol, and optionally has a branched structure or a cyclic structure.

21. The process according to claim 19, wherein the aliphatic alcohol is at least one of methanol, ethanol, 1-propanol, 2-propanol, 2-chloro-1-propanol, 1-chloro-2-propanol, 1-butanol, 2-butanol, isobutanol, tert-butanol, 1-pentanol, 2-methyl-1-butanol, 3-methyl-1-butanol, 2,2-dimethyl-1-propanol, cyclopentanol, 1-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, 3-ethyl-1-butanol, cyclohexanol, 1-octanol, 2-octanol, 2-ethyl-1-hexanol, 1-decanol, 2-decanol, 1-dodecanol, 2-dodecanol, 1-tetradecanol, 2-tetradecanol, 1-hexadecanol, 2-hexadecanol, 1-octadecanol, and 2-octadecanol.

22. The process according to claim 15, wherein the alcohol is a phenolic compound.

23. The process according to claim 22, wherein the phenolic compound has from 1 to 5 condensed aromatic rings.

24. The method of claim 22, wherein the phenolic compound is at least one of phenol, napthol, 1-hydroxyanthracene, 2-hydroxyanthracene, 1,4-dihydroxyanthracene, 1-hydroxyphenanthrene, 1-hydroxypyrene, hydroxybenzopyrene, hydroxypentacene, hydroxynaphtacene, and hydroxychrysene.

25. A pyrolysis oil product produced according to the process, comprising the steps:
   pyrolyzing a biomass, thereby generating a heated pyrolysis oil vapor comprising at least one carbonyl-containing component;
   delivering the pyrolysis oil vapor to a reactive condensation unit,
   delivering an atomized alcohol or amine to the reactive condensation unit, thereby forming a reaction mix comprising the pyrolysis oil vapor and the atomized alcohol or amine;
   maintaining the reaction mix under conditions suitable for generating at least one condensation reaction product in the absence of a catalyst, wherein the conditions allowing an esterification reaction between the carbonyl-containing component and the alcohol in the absence of a catalyst comprise a reaction time of about 40 secs to about 70 secs and a temperature of about 110° C. to about 130° C.; and
   condensing the pyrolysis oil vapor and the at least one condensation reaction product to form a pyrolysis oil product having an increased ester or amide content and increased stability when compared to a condensed pyrolysis oil product not treated with an atomized alcohol or amine.

26. The method of claim 25, wherein the amine is at least one of an alkyl amino, a dialkyl amino, an arylamino, a diarylamino, an alkylarylamino, an alkylaminoaryl, an arylaminoalkyl, and an alkaminoalkyl.

27. A system for generating a pyrolysis product, comprising:
   a pyrolysis unit configured to receive and pyrolyze a biomass, thereby generating a heated pyrolysis oil vapor having a carbonyl-containing component;
   a reactive condensation unit operably communicating with the pyrolysis unit, wherein the reactive condensation unit is configured to receive a liquid stream of an alcohol or amine and the reactive condensation unit further comprises an atomizing nozzle configured to atomize the received liquid stream of alcohol or amine, and wherein the reactive condensation unit is configured to allow a condensation reaction between the carbonyl-containing component and the alcohol or amine in the absence of a catalyst with a reaction time of about 40 secs to about 70 secs and a temperature of about 110° C. to about 130° C., thereby forming a reaction mix within the reactive condensation unit; and a receiving vessel operably disposed to receive from the reactive condensation unit a condensate comprising a pyrolysis oil product.

28. The system according to claim 27, wherein the pyrolysis unit further comprises a conveyor system disposed within said pyrolysis unit for continual passage of a biomass through the pyrolysis unit.

* * * * *